United States Patent
Kauffman et al.

(10) Patent No.: US 8,871,812 B2
(45) Date of Patent: *Oct. 28, 2014

(54) THERAPEUTIC REGIMEN COMPRISING PEG-INTERFERON, RIBAVIRIN AND VX-950 FOR THE TREATMENT OF HEPATITIS

(71) Applicants: Vertex Pharmaceuticals Incorporated, Boston, MA (US); Janssen Pharmaceutica NV, Beerse (BE)

(72) Inventors: Robert S. Kauffman, Chestnut Hill, MA (US); Cyril Jean Camille Titeux, Vienna (AT); Ramon Polo, Basking Ridge, NJ (US); Rudolf Peter Gerhard Van Heeswijk, Beerse (BE); Maria Gloria Beumont, Issy les Moulineaux (FR); Gaston Rafael Picchio, Flemington, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/718,608

(22) Filed: Dec. 18, 2012

(65) Prior Publication Data
US 2013/0101554 A1    Apr. 25, 2013

Related U.S. Application Data

(63) Continuation of application No. 13/070,991, filed on Mar. 24, 2011, now abandoned, and a continuation-in-part of application No. PCT/US2009/058218, filed on Sep. 24, 2009.

(60) Provisional application No. 61/099,849, filed on Sep. 24, 2008, provisional application No. 61/109,655, filed on Oct. 30, 2008, provisional application No. 61/243,041, filed on Sep. 16, 2009.

(51) Int. Cl.
A61K 38/21    (2006.01)
A61K 38/00    (2006.01)
A61K 31/14    (2006.01)
A61K 38/07    (2006.01)
A61K 31/7056  (2006.01)

(52) U.S. Cl.
CPC .............. *A61K 38/212* (2013.01); *A61K 38/07* (2013.01); *A61K 31/7056* (2013.01); *Y10S 514/894* (2013.01)

USPC .......... 514/588; 514/4.3; 514/894; 424/85.7; 424/85.4

(58) Field of Classification Search
None
See application file for complete search history.

(56) References Cited

FOREIGN PATENT DOCUMENTS

WO    2005123076 A    12/2005
WO    2008144072 A    11/2008

OTHER PUBLICATIONS

Reesink, H.W., et al., Rapid Decline of Viral RNA in Hepatitis C Patients Treated With VX-950: A Phase Ib, Placebo-Controlled, Randomized Study, Gastroenterology, 2006, pp. 997-1002, vol. 131, No. 4, American Gastroenterological Association (AGA) Institute.
Lawitz, E.J., et al., 28 Days of the Hepatitis C Protease Inhibitor VX-950, in Combination With PEG-Interferon-ALFA-2a and Ribavirin, is Well-Tolerated and Demonstrates Robust Antiviral Effects, Gastroenterology, Sep. 2006, pp. 950-951, vol. 131, No. 3, AGA Institute.
Revill, P., et al., Telaprevir, HCV NS3 Protease Inhibitor Treatment of Hepatitis C, Drugs of the Future, 2007, pp. 788-798, vol. 32, No. 9, Prous Science.
Vertex Pharmaceuticals Incorporated, Researchers Report Results for 28-day Phase II Study of VX-590 in Combination with Pegylated interferon and Ribavirin in Hepatitis C C Patients, 2008.
McHutchison, J.G., et al, Results of an Interim Analysis of a Phase 2 Study of Telaprevir (VX-950) with Peginterferon alpha-2a and Ribavirin in Previously Untreated Subjects with Hepatitis C, Late-Breaking Abstracts, J. of Hepatology, Apr. 2007, p. S296, vol. 46.
VX-950-TIDP24-C208: An Open-Label Study of Telaprevir Administered Every 12 or Every 8 Hours in Combination With Standard Treatment in Treatment naive Patients With Chronic Genotype 1 Hepatitis C, ClinicalTrials.gov archive, Sep. 11, 2007, http://clinicaltrials.gov/archive/NCT00528528/2007_09_11.
Keefe et al., Latest Breakthroughs in Chronic Hepatitis B and C, Rev. Gastroent. Disord., 2007, pp. 167-175, vol. 7, No. 3.

*Primary Examiner* — Christine J Saoud
*Assistant Examiner* — Jegatheesan Seharaseyon
(74) *Attorney, Agent, or Firm* — Honigman Miller Schwartz & Cohn; Noel E. Day; Jonathan P. O'Brien

(57) ABSTRACT

The present invention relates to antiviral therapies and compositions for treating or preventing Hepatitis C infections in patients and relates to other methods disclosed herein. The invention also relates to kits and pharmaceutical packs comprising compositions and dosage forms.

26 Claims, 4 Drawing Sheets

SEQUENCE LISTING

```
<160> NUMBER OF SEQ ID NOS: 1

<210> SEQ ID NO 1
<211> LENGTH: 10
<212> TYPE: PRT
<213> ORGANISM: Hepatitis C virus
<220> FEATURE:
<221> NAME/KEY: MISC_FEATURE
<222> LOCATION: (5)..(5)
<223> OTHER INFORMATION: Xaa is abu defined as aminobutyric acid

<400> SEQUENCE: 1

Glu Asp Val Val Xaa Cys Ser Met Ser Tyr
1               5                   10
```

THERAPEUTIC REGIMEN COMPRISING PEG-INTERFERON, RIBAVIRIN AND VX-950 FOR THE TREATMENT OF HEPATITIS

CROSS-REFERENCE

This application is a continuation of U.S. application Ser. No. 13/070,991, filed on Mar. 24, 2011, which is a continuation of PCT Application No. PCT/US2009/058218, filed on Sep. 24, 2009, which claims priority to U.S. Application Ser. No. 61/099,849, filed Sep. 24, 2008, U.S. Application Ser. No. 61/109,655, filed Oct. 30, 2008, and U.S. Application Ser. No. 61/243,041, filed Sep. 16, 2009, the contents of which are incorporated herein by reference in their entireties.

Incorporated herein by reference is a Sequence Listing named "08-146PCT_ST25.txt" created on Sep. 24, 2009, that is 761 bytes. The sequence listing does not include any new matter which goes beyond the disclosure of the application as filed.

TECHNICAL FIELD OF THE INVENTION

The present invention relates to methods for treating Hepatitis C virus infections.

BACKGROUND OF THE INVENTION

Infection by Hepatitis C virus (HCV) is a compelling human medical problem. HCV is recognized as the causative agent for most cases of non-A, non-B hepatitis, with an estimated human sero-prevalence of 3% globally. Nearly four million individuals may be infected in the United States alone.

Of persons who become infected with HCV, 20-25% may be able to clear the virus after the acute infection, but 75-80% will develop chronic Hepatitis C infection. This usually results in recurrent and progressively worsening liver inflammation, which often leads to more severe disease states such as cirrhosis and hepatocellular carcinoma. Unfortunately, there are no broadly effective treatments for the debilitating progression of chronic HCV.

The HCV genome encodes a polyprotein of 3010-3033 amino acids. The HCV nonstructural (NS) proteins are presumed to provide the essential catalytic machinery for viral replication. The NS proteins are derived by proteolytic cleavage of the polyprotein.

The HCV NS protein 3 (NS3) contains a serine protease activity that helps process the majority of the viral enzymes, and is thus considered essential for viral replication and infectivity. It is known that mutations in the yellow fever virus NS3 protease decreases viral infectivity. The first 181 amino acids of NS3 (residues 1027-1207 of the viral polyprotein) have been shown to contain the serine protease domain of NS3 that processes all four downstream sites of the HCV polyprotein.

The HCV NS3 serine protease and its associated cofactor, NS4A, helps process all of the viral enzymes, and is thus considered essential for viral replication. This processing appears to be analogous to that carried out by the human immunodeficiency virus aspartyl protease, which is also involved in viral enzyme processing. HIV protease inhibitors, which inhibit viral protein processing are potent antiviral agents in man, indicating that interrupting this stage of the viral life cycle results in therapeutically active agents. Consequently it is an attractive target for drug discovery.

There are not currently any satisfactory anti-HCV agents or treatments. Until recently, the only established therapy for HCV disease was interferon treatment. The first approved therapy for HCV infection was treatment with standard (non-pegylated) interferon alfa. However, interferons have significant side effects and interferon alfa monotherapy induces long term remission in only a fraction (~25%) of cases. The addition of ribavirin to the treatment regimen increases response rates slightly. Recent introductions of the pegylated forms of interferon (PEG-INTRON® and PEGASYS®), which has also been combined with ribavirin have resulted in only modest improvements in remission rates and only partial reductions in side effects. (PEG refers to polyethyleneglycol.) The current standard of care is a treatment regimen lasting 24-48 weeks, depending on prognostic factors such as HCV genotype and demonstration of initial response to therapy. The majority of HCV genotype-1 patients do not achieve sustained virologic response (SVR) after a 48-week regimen of pegylated interferon-alfa-2a/2b and ribavirin. Moreover, retreatment of prior PR non-responders (null and partial responders) and relapsers with pegylated interferon and ribavirin achieves SVR rates of less than 10% and 30%, respectively. The prospects for effective anti-HCV vaccines remain uncertain.

Thus, there is a need for anti-HCV therapies and appropriate dose regimens for anti-HCV compounds.

HCV and other diseases and disorders are associated with liver damage. There is also a need for therapies and appropriate dose regimens for treating liver damage.

SUMMARY OF THE INVENTION

The present invention provides a treatment for Hepatitis C virus infections. In one embodiment, the present invention is directed to a therapeutic regimen comprising administering to a patient peginterferon and ribavirin with VX-950 in an initial phase and administering peginterferon and ribavirin over a secondary phase, wherein the secondary phase occurs after the initial phase, and wherein VX-950 is administered in an amount of 1125 mg twice per day, peginterferon is administered in an amount of 180 micrograms per week and ribavirin is administered in an amount of 1000 to 1200 mg per day.

In another embodiment, the present invention is directed to a therapeutic regimen comprising administering to a patient peginterferon and ribavirin with VX-950 in an initial phase and administering peginterferon and ribavirin over a secondary phase, wherein the secondary phase occurs after the initial phase, and wherein VX-950 is administered in an amount of 1125 mg twice per days, peginterferon is administered in an amount of 1.5 micrograms per kilogram per week and ribavirin is administered in an amount of 800 to 1200 mg per day.

DETAILED DESCRIPTION OF THE INVENTION

Figure 1:
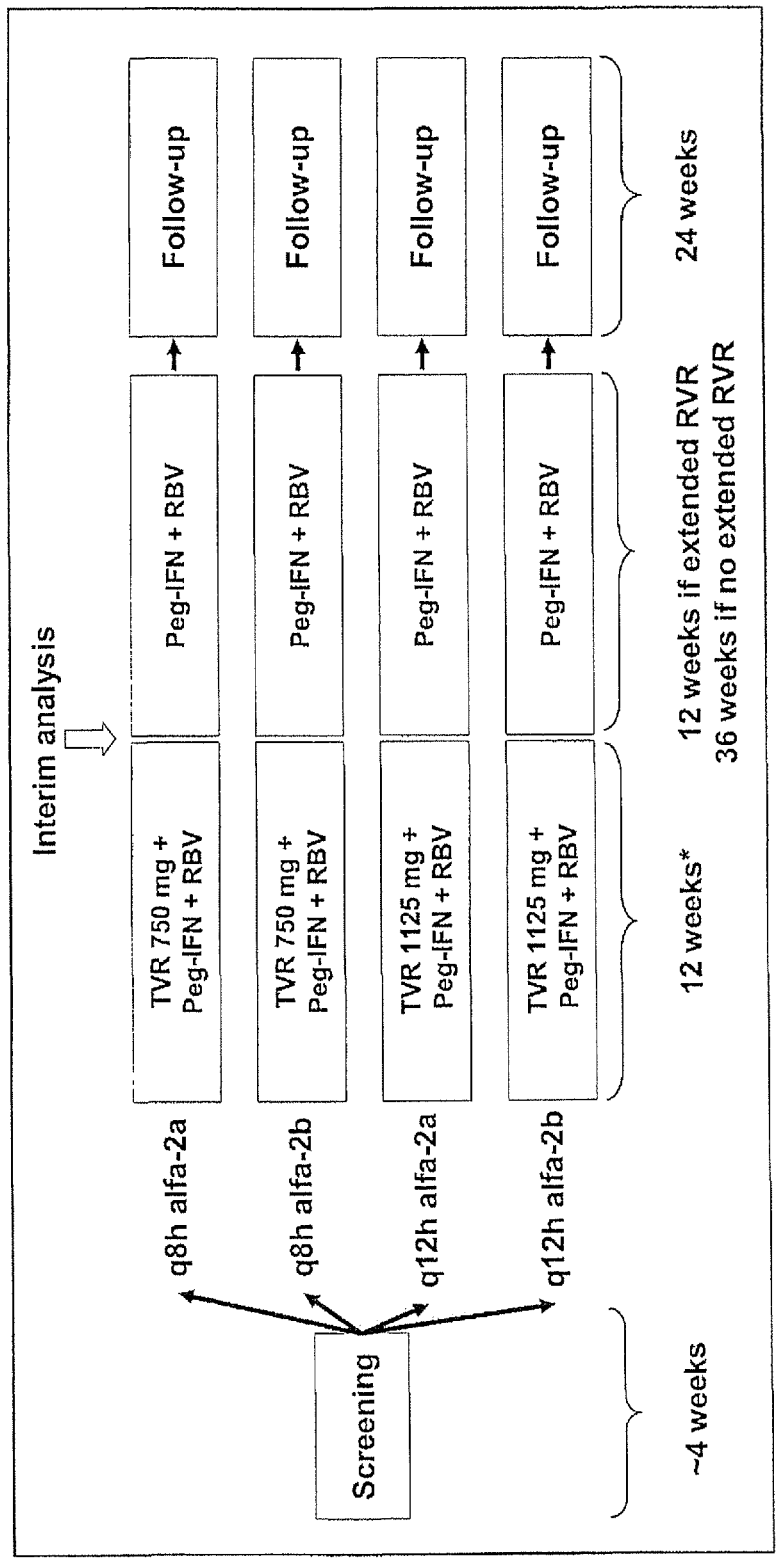
FIG. 1 depicts the C208 study design.
Figure 2:
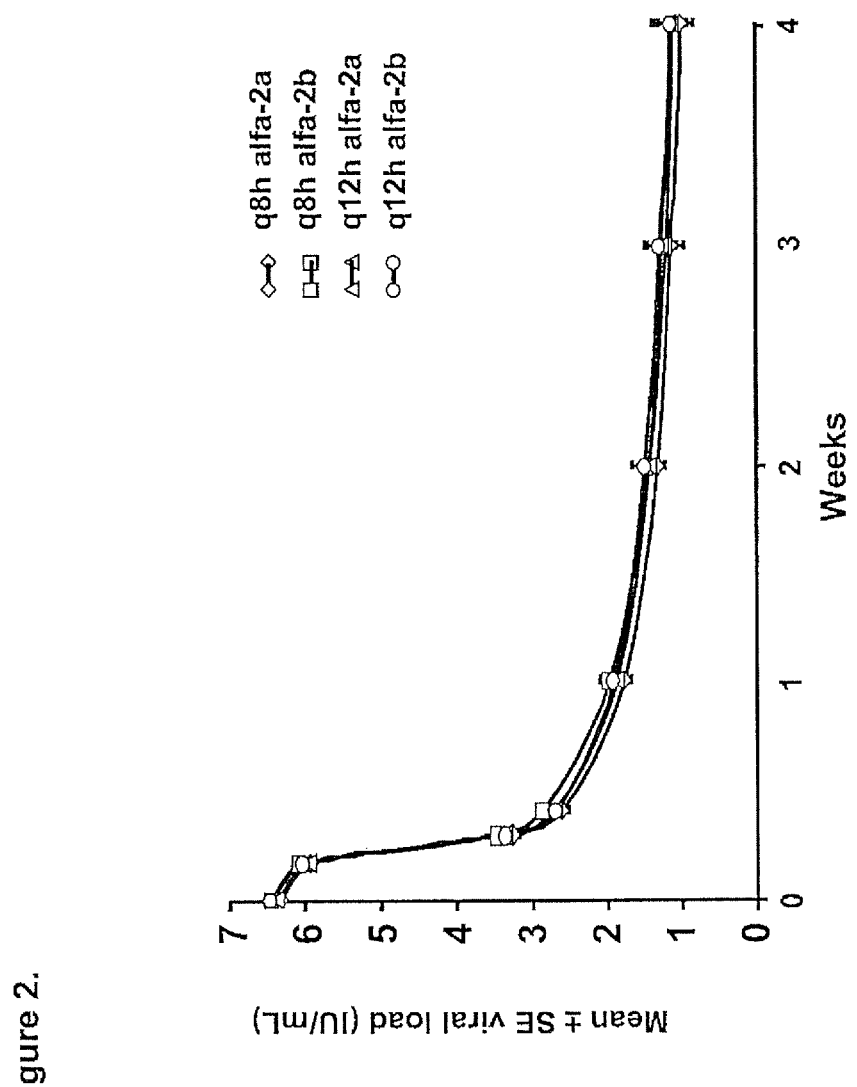
FIG. 2 depicts the mean change in $\log_{10}$ HCV RNA levels over time (NC=F).
Figure 3:
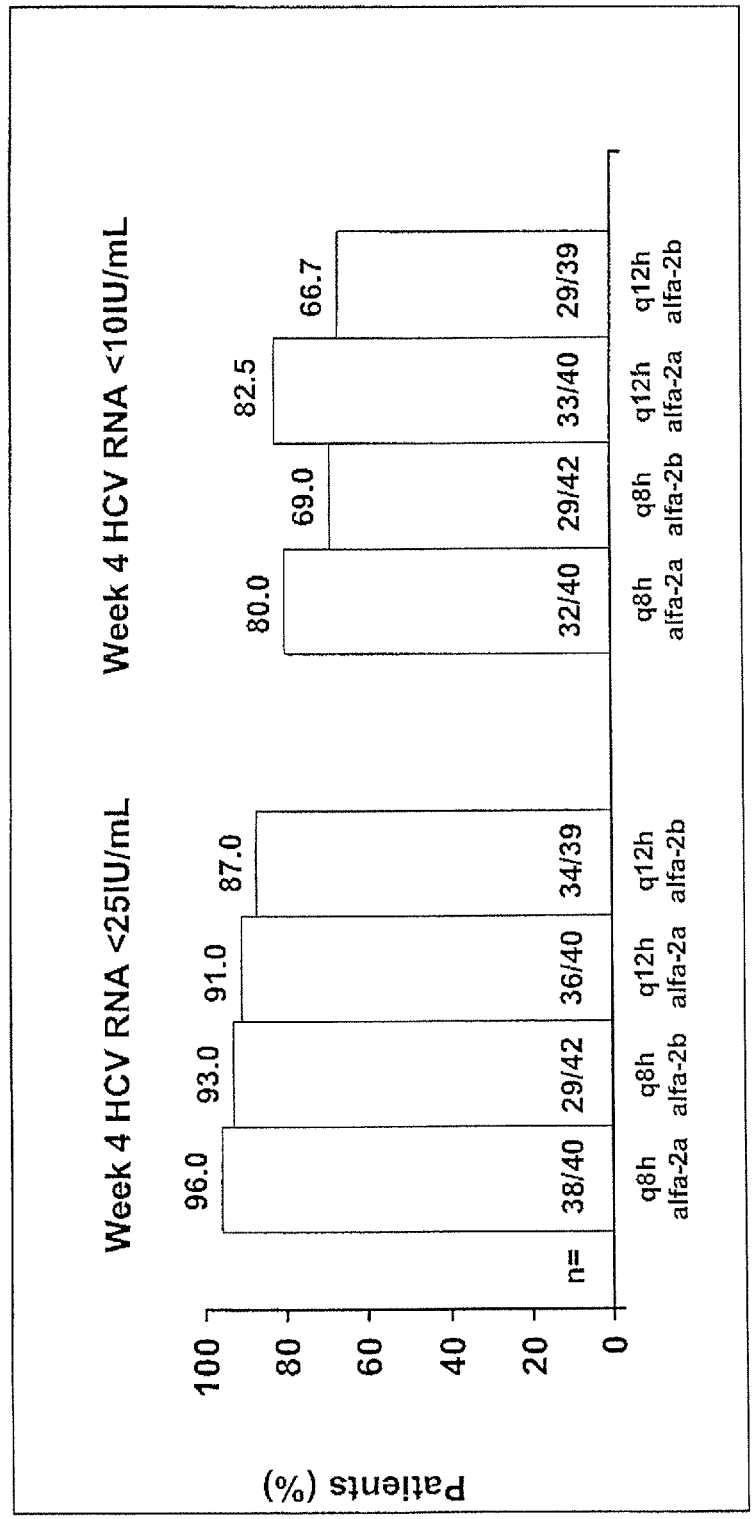
FIG. 3 depicts the virologic response rate at week 4.
Figure 4:
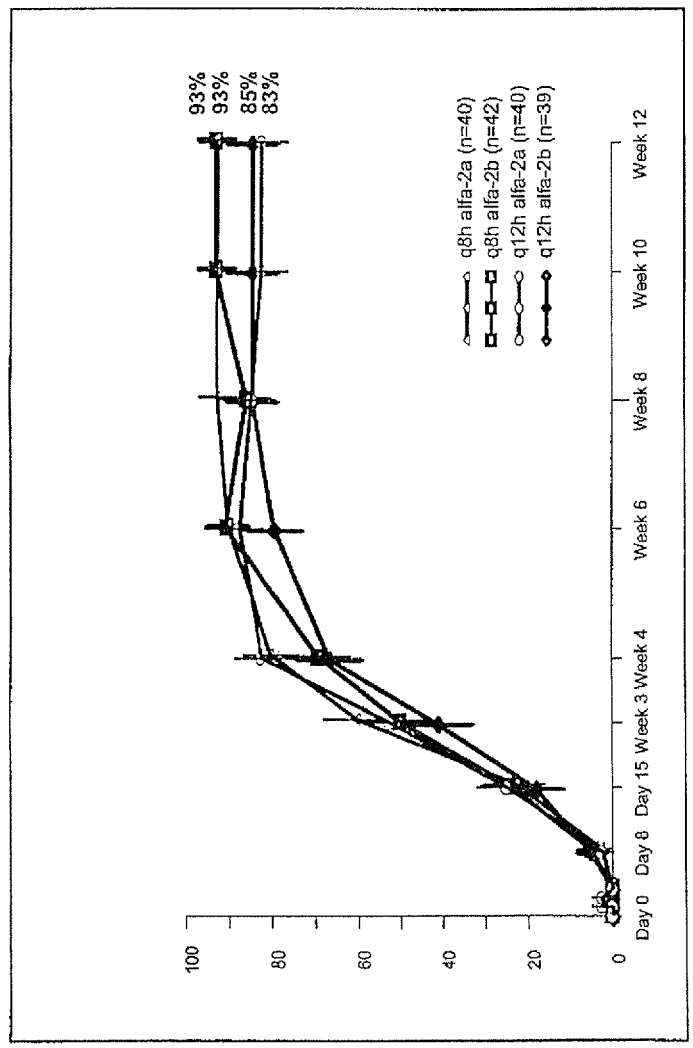
FIG. 4 depicts the % of patients with undetectable HCV RNA (<10 IU/mL).

VX-950 is described in PCT Publication Numbers WO 02/018369, WO 2006/050250 and WO/2008/144072, with reference to the following structural formula, or a pharmaceutically acceptable salt thereof:

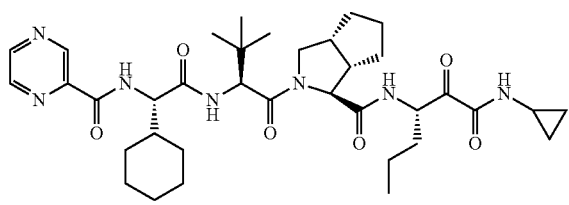

(I)

Other descriptions of VX-950 can be found in PCT Publication Numbers WO 07/098,270 and WO 08/106,151.

Accordingly, one embodiment of this invention provides a therapeutic regimen comprising administering to a patient VX-950 and a pharmaceutically acceptable carrier. The amount of VX-950 in these pharmaceutical compositions can be from about 100 mg to about 1500 mg, from about 300 mg to about 1500 mg, from about 300 mg to about 1250 mg, about 450 mg, about 750 mg, or about 1250 mg. Each of these pharmaceutical compositions can be administered, e.g., once, twice, or three times per day. Each of these compositions can be in one or more dosage forms (e.g., ampule, capsule, cream, emulsion, fluid, grain, drop, injection, suspension, tablet, powder). Each of these pharmaceutical compositions can be administered by one or more routes (e.g., orally, by infusion, by injection, topically, or parenterally) as considered appropriate by a skilled person in the art and depending on the dosage form.

Another aspect of this invention provides a method for treating or preventing HCV infections of a patient which includes administering to the patient VX-950.

In some embodiments, the amount of VX-950 is at least about 300 mg (e.g., at least about 450 mg, at least about 500 mg, at least about 750 mg, at least about 1250 mg, or at least about 1500 mg). In some embodiments, the amount of VX-950 is no more than about 1500 mg (e.g., no more than about 1250 mg, no more than about 750 mg, no more than about 450 mg, no more than about 500 mg, or no more than about 300 mg).

It should be understood that these lower and upper amounts may be combined to provide preferred dose ranges for administering VX-950. For example, in some embodiments, VX-950 is administered in an amount from about 300 mg to about 1250 mg or from about 300 mg to about 1500 mg.

In some embodiments, VX-950 is administered in an amount of about 450 mg. In other embodiments, VX-950 is administered in an amount of about 500 mg. In other embodiments, VX-950 is administered in an amount of about 600 mg. In other embodiments, VX-950 is administered in an amount of about 750 mg. In other embodiments, VX-950 is administered in an amount of about 1000 mg. In other embodiments, VX-950 is administered in an amount of about 1250 mg.

In any of these embodiments, the specified amount of VX-950 is administered once a day. Alternatively, the amount of VX-950 is administered twice a day (e.g., BID; q12h). Alternatively, the amount of VX-950 is administered three times a day (e.g., TID; q8h). Further, VX-950 may be administered with or without food.

VX-950 has also been tested in humans and found to be effective at inhibiting HCV replication. Applicants have demonstrated that administration of VX-950 was able to substantially decrease HCV RNA levels. Importantly, applicants have demonstrated that administration of VX-950 to subjects infected with HCV can inhibit the virus such that the viral RNA becomes undetectable using the Roche COBAS TAQ-MAN ™ HCV/HPS assay (available from Roche Molecular Diagnostics). In previous studies, of 8 subjects receiving 750 mg of VX-950 every 8 hours (q8h), 4 had HCV RNA levels below the limit of quantitation (LLQ 30 IU/mL) and 2 of those 4 subjects had HCV RNA levels below the limit of detection (LLD 10 IU/mL).

In previous studies, subjects receiving 750 mg of VX-950 every eight hours for 14 days achieved a median reduction in HCV-RNA of greater than 4 $\log_{10}$ (i.e., 10,000-fold decrease) at the end of the treatment. A median reduction of HCV-RNA of greater than 2 $\log_{10}$ was seen in each of the other two VX-950 dose groups at the end of 14 days of treatment. Every subject receiving VX-950 achieved greater than a 2 $\log_{10}$) reduction in HCV-RNA within the first three days of treatment, and 26 of the 28 subjects receiving VX-950 had a 3 $\log_{10}$ reduction in HCV-RNA within the first three days of treatment. See, Example 5.

It was demonstrated that plasma viral loads decline rapidly in patients treated with VX-950. Additionally, it was demonstrated that there was a slow return towards baseline HCV RNA levels after the end of dosing. Specifically, the rate of return to HCV RNA baseline levels following the end of treatment was slower than the rate of decline of HCV RNA upon treatment. These results, together with achieving undetectable HCV RNA levels, indicate the effectiveness of VX-950 as a monotherapy.

Accordingly, VX-950, or a pharmaceutically acceptable salt thereof, may be administered to a patient infected with HCV in an amount of: a) about 450 mg, 3 times per day, every 8 hours; b) in an amount of about 750 mg, 3 times per day, every 8 hours; c) in an amount of about 1250 mg, 2 times per day, every 12 hours; or d) in an amount of about 1250 mg each time, 3 times per day, every 8 hours.

In other embodiments, this invention provides a method for treating a patient infected with HCV, comprising administering to the patient VX-950, or a pharmaceutically acceptable salt thereof, in an amount of about 1125 mg, two times per day; or in an amount of about 1125 mg, every 12 hours.

In other embodiments, this invention provides a method for treating a patient infected with HCV by administering VX-950 such that the level of HCV RNA in the patient is at least about 2 $\log_{10}$ (e.g., at least about 4 $\log_{10}$) lower than before treatment.

Yet still another aspect of this invention provides a method for treating a patient infected with HCV by administering VX-950 such that the level of viral RNA in the patient decreases to an undetectable level and remains at that undetectable level until a "sustained viral response" is achieved.

Generally, the terms "RVR," "SVR," "EVR" are well known in the art and within the meaning well accepted in the art. For example, "RVR" means rapid viral response, "SVR" means sustained viral response, and "EVR" means early viral response. Typically, "RVR" indicates an undetectable HCV RNA level at week 4; "SVR" indicates an undetectable HCV RNA level 48 weeks after the end of treatment; and "EVR" indicates ≥2-log10 reduction from baseline in HCV RNA at week 12 or undetectable HCV RNA at week 12. As described above, HCV RNA being "undetectable" means that the HCV RNA is present in less than 10 IU/mL as determined by assays currently commercially available, and preferably as determined by the Roche COBAS TAQMAN ™ HCV/HPS assay.

It has been shown that a method of this invention that employs 750 mg of VX 950 every 8 hours results in higher trough levels. The trough level is the concentration that a drug drops down to in plasma just before next dose (i.e., the minimum concentration between doses). It is important, particularly in viral diseases, to maintain drug levels above a certain concentration to maintain appropriate inhibition of viral replication.

Accordingly, in a preferred embodiment, this invention provides a method for administering VX-950 to a patient in need thereof, which includes administering the compound in an amount of about 750 mg each time, 3 times per day, once every 8 hours.

As would be recognized, it is advantageous to have flexible dosing schedules. Accordingly, in another embodiment of this invention, the administration is 3 times per day, but not every 8 hours, optionally with meals. In certain embodiments, VX-950 is administered with food.

This invention also provides a method for providing VX-950 to a patient in need thereof, which includes administering to the patient an oral dose of a composition comprising VX-950, wherein said dose provides to the patient an average plasma concentration ($C_{avg}$) of VX-950 of at least about 750 ng/mL after the administration. In some embodiments, the $C_{avg}$ of VX-950 is about 1000 ng/mL or about 1250 ng/mL. In some embodiments, said dose essentially contains about 750 mg of VX-950. In some embodiments, the $C_{avg}$ is obtained/attained within 3 hours after administration, preferably 2 hours, more preferably 1 hour after administering. In a preferred form of these embodiments, the $C_{avg}$ of VX-950 is maintained over about 24 hours, and preferably over 12 weeks.

In another aspect, this invention provides a method for treating HCV infection in a patient by administering at least one dosage form comprising VX-950 over a 24-hour period, wherein the dosage form is administered to maintain a trough plasma VX-950 level minimum of about 750 ng/ml over the 24-hour period.

In certain forms of this embodiment, the dosage form is administered to maintain a trough plasma VX-950 level minimum of about 800 ng/mL, preferably about 900 ng/ml over the 24 hour period, and more preferably about 1000 ng/mL over the 24 hour period.

In certain preferred embodiments a therapeutically effective plasma concentration is obtained and a certain trough level is maintained. These methods are particularly useful for treating a human suffering from HCV infection by administering a VX-950 formulation, wherein the trough VX-950 plasma level is maintained at a minimum of about 750, 800, 900, or 1000 ng/mL over a 24 hour period. Without being bound by theory, trough levels of more than about 1500 ng/mL are thought to be not required by this invention. Accordingly, trough levels of about 750, 800, 900, 1000 ng/mL to about 1500 ng/mL (particularly 1000 to about 1500) are within the scope of this invention.

Also provided is a dosage form for delivering VX-950 to a human, wherein the dosage form comprises VX-950, said dosage form when administered at least once during a 24 hour period maintains a trough plasma VX-950 level that is at least about 750 ng/mL, 800 ng/mL, 900 ng/mL, or 1000 ng/mL over the 24 hour period to about 1500 ng/mL (particularly 1000 ng/mL to about 1500 ng/mL) over the 24 hour period.

Ideally, when a method of this invention involves treating a patient infected with HCV, the method involves achieving, relatively rapidly, a therapeutically effective plasma concentration of VX-950 and then maintaining the trough level such that an effective therapeutic response is achieved. An effective therapeutic response is, preferably, one or both of a) achieving a sustained viral response; and b) achieving undetectable HCV RNA in the plasma by at least 12 weeks (12 weeks or more). As used herein, HCV RNA being "undetectable" means that the HCV RNA is present in less than 10 IU/mL as determined by assays currently commercially available, and preferably as determined by the Roche COBAS TAQMAN™ HCV/HPS assay.

The relatively rapid drop in plasma concentration may be obtained by administering a loading dose to a patient. In one embodiment, the loading dose is about 1250 mg of VX-950.

In certain dosage forms of this invention, the dosage form (other than the dosage form used to administer the loading dose) contains about 750 mg of VX-950 and the dosage form is administered once every 8 hours (i.e., q8h).

In certain embodiments, the VX-950 dosage form is administered once every 8 hours.

In certain embodiments, the VX-950 dosage form is administered once every 12 hours.

In certain embodiments, the treatment duration with VX-950 is shorter than the current standard of care.

In certain embodiments, VX-950 is administered for less than about 12 weeks (or less than 12 weeks).

In certain embodiments, VX-950 is administered for about 8-12 weeks (or 8-12 weeks).

In certain embodiments, VX-950 is administered for about 10 weeks (or 10 weeks).

Modeling data indicate that administration with VX-950 may eradicate wild-type virus within 10 weeks.

In certain embodiments, VX-950 is administered for less than about 10 weeks.

In certain embodiments, VX-950 is administered for about 2 weeks.

Applicants have demonstrated that SVR was achieved in a patient receiving a 2 week treatment of VX-950.

In other embodiments, VX-950 is administered for less than about 8 weeks (or about 8 weeks or 8 weeks), less than about 6 weeks (or about 6 weeks or 6 weeks), or less than about 4 weeks (or about 4 weeks or 4 weeks).

In certain embodiments, a method according to this invention involves the treatment of a patient infected with genotype 1 Hepatitis C virus. Genotype 1 HCV infection is the most difficult strain of HCV to treat and the most prevalent strain in the United States.

Applicants have also demonstrated that administration of VX-950 decreases neopterin and ALT levels in vivo. AST (aspartate aminotransferase) levels were also decreased upon administration of VX-950. ALT is an enzyme that is present in liver cells; when liver cells are damaged or inflamed, ALT leaks from the cell into the blood. Blood ALT levels are useful as a marker of liver inflammation or damage.

Neopterin (6-d-erythro-trihydroxypropylpteridine) is a pteridine derivative that is produced during the metabolism of guanosine triphosphate (GTP). Neopterin is produced primarily by monocytes and macrophages upon activation by interferon gamma or interferon alfa and is a marker of inflammation. Neopterin levels are frequently elevated in chronic HCV infection. The expected plasma level of neopterin in healthy individuals is between 3.1 and 7.7 nmol/l.

Accordingly, applicants determined the changes in serum neopterin concentration as a marker of monocyte/macrophage activity during administration of an inhibitor of (HCV) NS3·4A protease. As described herein, VX-950 was administered for 14 days in a randomized, double blind, placebo controlled, multiple-dose study in 34 patients infected with HCV genotype 1. Patients received VX-950 450 mg q8h (n=10), 750 mg q8h (n=8), 1250 mg q12h (n=10), or placebo (n=6). Serum neopterin concentrations were measured by a quantitative competitive ELISA (ELItest® Neopterin, Brahms, Hennigsdorf, Germany) at pretreatment, at day 7 and 14, and at day 10 of follow-up. The lower limit of detection (LLD) was 2 nmol/l. HCV RNA was assessed at frequent intervals during the study by real-time PCR (COBAS TAQ-MAN™ HCV Test; linear dynamic range of $3.0 \times 10^1$ to $2.0 \times 10^8$ HCV RNA IU/ml; LLD of 10 HCV RNA IU/ml; Roche Diagnostics, Branchburg, N.J.).

During administration of VX-950, every patient demonstrated at least $2\text{-log}_{10}$ drop in viral load in all dose groups. In the 750 mg q8h dose group, mean HCV RNA dropped 3.6 $\log_{10}$ at day 3, and 4.3 $\log_{10}$ at day 14. In the 450 mg q8h and 1250 mg q12h dose groups, maximal effect was seen at day 3 to day 7 followed by an increase in mean viral load between day 7 and day 14. Mean viral loads increased in all dose groups during follow-up. Advantageously, both HCV treatment naïve and previously treated patients benefit from the methods of this invention. Both prior-treated patients and treatment naïve patients responded to VX-950. For the avoidance of doubt, patients that may be treated according to the methods of this invention include those where HCV treatment has not been tried or has failed, including non-responding, rebound, relapse, and breakthrough patients.

Baseline neopterin was elevated in 23/34 patients (mean 9.33 nmol/L; upper limit of normal (ULN) 7.7 nmol/l). In the 750 mg dose group the decrease in neopterin compared to baseline and to placebo became significant at day 14 (750 mg q8h dose group baseline v day 14 10.48±0.84 mmol/L v 7.32±0.48 nmol/L P=0.0104, Mann Whitney test; 750 mg q8h dose group v placebo day 14 7.32±0.48 nmol/l v 9.81±1.36 nmol/l P=0.0036, unpaired two-tailed T test). Mean neopterin levels were within normal values at day 14 only in the 750 mg q8h dose group. In the 450 mg q8h dose group and the 1250 mg q12h dose group, decreases in mean neopterin levels were smaller. Mean neopterin levels did not change in the placebo group. Mean neopterin levels increased in all dose groups during follow-up.

The serum alanine aminotransferase (ALT) level can be measured using commercially available methods. Mean ALT levels, elevated at baseline, decreased during dosing in all groups. Mean ALT levels increased, returned toward baseline, in all dose groups during follow up.

Although HCV RNA increased in the 450 mg dose group and 1250 mg dose group after day 7, neopterin and especially ALT continued to decrease. Changes in mean neopterin concentration correlated with decline in HCV RNA and ALT levels during dosing of VX-950. Maximal decline in mean neopterin concentration was in the 750 mg q8h dose group at day 14. This was also the dose group with maximal reductions in HCV RNA at day 14. After day 7 in the 450 mg q8h and 1250 mg q12h dose groups, ALT and neopterin levels decreased while HCV RNA levels increased. These data suggest that inhibition of HCV replication by VX-950 results in a marked decline in systemic inflammatory activity associated with viral infection.

VX-950 also ameliorates elevated ALT levels in an animal model (see WO 2005/025517). Specifically, expression of WT-HCV protease-SEAP in SCID mice results in elevated ALT levels that can be ameliorated by treatment with VX-950. Expression of WT-HCV protease alone in SCID mice also results in time and dose dependent elevation of ALT levels.

Accordingly, this invention provides a method for decreasing (including normalizing) ALT levels in a patient. The method includes administering to the patient in need thereof a therapeutically effective amount of VX-950 (e.g., about 1350 mg daily, about 2250 mg daily, or about 2500 mg daily). The patient can be infected with HCV or not infected with HCV.

In some embodiments, VX-950 is administered daily at about 450 mg or at about 750 mg every 8 hours, or at about 1250 mg every 12 hours.

Another aspect of this invention provides methods for treating or preventing one or more of liver damage, liver inflammation, steatosis, fatty liver, NAFLD, NASH, alcoholic steatosis, and Reye's syndrome in a patient that is either HCV positive or HCV negative.

Also within the scope of this invention are methods for hepatoprotection in a patient that is either HCV positive or negative.

Applicants have also demonstrated that VX-950 blocks immune evasion in vitro. VX-950 restores IFN dependent gene expression in Sendai virus infected Huh7 cells. IFNβ promoter activity decreases in response to Sendai virus stimulation in the presence of WT HCVpro. VX-950 overcomes the WT HCVpro mediated suppression of IFNβ promoter activation.

Furthermore, NS3/4A is known to be involved in evasion of innate defenses, by e.g., TRIF-dependent mechanisms (as well as viral polyprotein processing). This immune evasion leads to viral persistence. Accordingly, a compound that inhibits both viral polyprotein processing and evasion of innate defenses is desirable. Advantageously, VX-950 has been shown to do both. In particular, VX-950 inhibits in vitro cleavage of TRIF, which is a TLR3 adaptor protein.

Without being bound by theory, modeling suggests that VX-950 inhibits TRIF cleavage by NS3 protease. TRIF binds to non-prime side of the NS3 protease active site. VX-950 binds to the same non-prime side of the active site as TRIF and blocks TRIP cleavage.

It has been shown that two VX-950 viral variants, A156T and A156V, show reduced ability to cleave either TRIF or 4A/4B. Because these viral variants are less fit, they are inefficient at both viral polyprotein processing and viral persistence. Without being bound by theory, this is related to steric hindrance of A156V affecting binding to 4A/4B and TRIF substrates.

This indicates that VX-950 acts as both a direct antiviral and as an inhibitor of immune evasion. Accordingly, this invention also provides methods of inhibiting HCV protease mediated evasion of host defenses.

These results together with the in vivo data disclosed herein indicate the effectiveness of VX-950 as a monotherapy.

The amounts of VX-950 according to this invention are administered in a single dosage form or in more than one dosage form. If in separate dosage forms, each dosage form is administered about simultaneously. For the avoidance of doubt, for dosing regimens calling for dosing more than once a day, one or more pill or dose may be given at each time per day (e.g., 1 pill, three times per day or 3 pills, three times per day). Most embodiments of this invention will employ at least 2 pills per dose).

As would be realized by skilled practitioners, if a method of this invention is being used to treat a patient prophylactically, and that patient becomes infected with Hepatitis C virus, the method may then treat the infection. Therefore, one embodiment of this invention provides methods for treating or preventing a Hepatitis C infection in a patient.

In addition to treating patients infected with Hepatitis C, the methods of this invention may be used to prevent a patient from becoming infected with Hepatitis C. Accordingly, one embodiment of this invention provides a method for preventing a Hepatitis C virus infection in a patient comprising administering to the patient a composition or dosage form according to this invention.

The data disclosed herein indicate the effectiveness of VX-950 as a combination therapy.

Methods of this invention may also involve administration of another component comprising an additional agent selected from an immunomodulatory agent; an antiviral agent; an inhibitor of HCV protease (other than VX-950); an inhibitor of another target in the HCV life cycle (other than NS3/4A protease); an inhibitor of internal ribosome entry, a broad-spectrum viral inhibitor; or a cytochrome P-450 inhibitor; or combinations thereof. The additional agent is also selected from an inhibitor of viral cellular entry.

Such anti-viral agents include, but are not limited to, immunomodulatory agents, such as α-, β-, and γ-interferons or thymosin, pegylated derivatized interferon-α compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the HCV life cycle, including helicase, polymerase, and metalloprotease inhibitors; inhibitors of internal ribosome entry; broad-spectrum viral inhibitors, such as IMPDH inhibitors (e.g., compounds described in U.S. Pat. Nos. 5,807,876, 6,498,178, 6,344,465, and 6,054,472; and PCT publications WO 97/40028, WO 98/40381, and WO 00/56331; and mycophenolic acid and derivatives thereof, and including, but not limited to, VX-497, VX-148, and VX-944); or any of their combinations.

Other agents (e.g., non-immunomodulatory or immunomodulatory compounds) may be used in combination with a compound of this invention include, but are not limited to, those specified in WO 02/18369, which is incorporated herein by reference (see, e.g., page 273, lines 9-22 and page 274, line 4 to page 276, line 11 this disclosure being specifically incorporated herein by reference).

Still other agents include those described in various published U.S. patent applications. These publications provide additional teachings of compounds and methods that could be used in combination with VX-950 in the methods of this invention, particularly for the treatment of hepatitis. It is contemplated that any such methods and compositions may be used in combination with the methods and compositions of the present invention. For brevity, the disclosure the disclosures from those publications is referred to be reference to the publication number but it should be noted that the disclosure of the compounds in particular is specifically incorporated herein by reference. Examples of such publications include U.S. Patent Application Publication Nos.: US 20040058982, US 20050192212, US 20050080005, US 20050062522, US 20050020503, US 20040229818, US 20040229817, US 20040224900, US 20040186125, US 20040171626, US 20040110747, US 20040072788, US 20040067901, US 20030191067, US 20030187018, US 20030186895, US 20030181363, US 20020147160, US 20040082574, US 20050192212, US 20050187192, US 20050187165, US 20050049220, and US 20050222236.

Still other agents include, but are not limited to, Albuferon™ (albumin-Interferon alpha) available from Human Genome Sciences; PEG-INTRON® (peginterferon alfa-2b, available from Schering Corporation, Kenilworth, N.J.); INTRON-A®, (VIRAFERON®, interferon alfa-2b available from Schering Corporation, Kenilworth, N.J.); ribavirin (1-beta-D-ribofuranosyl-1H-1,2,4-triazole-3-carboxamide, available from ICN Pharmaceuticals, Inc., Costa Mesa, Calif.; described in the Merck Index, entry 8365, Twelfth Edition); REBETROL® (Schering Corporation, Kenilworth, N.J.); COPEGUS® (Hoffmann-La Roche, Nutley, N.J.); PEGASYS® (peginterferon alfa-2a available Hoffmann-La Roche, Nutley, N.J.); ROFERON® (recombinant interferon alfa-2a available from Hoffmann-La Roche, Nutley, N.J.); BEREFOR® (interferon alfa 2 available from Boehringer Ingelheim Pharmaceutical, Inc., Ridgefield, Conn.); SUMIFERON® (a purified blend of natural alpha interferons such as Sumiferon available from Sumitomo, Japan); WELLFERON® (interferon alpha n1 available from Glaxo Wellcome Ltd., Great Britain); ALFERON® (a mixture of natural alpha interferons made by Interferon Sciences, and available from Purdue Frederick Co., CT); α-interferon; natural alpha interferon 2a; natural alpha interferon 2b; pegylated alpha interferon 2a or 2b; consensus alpha interferon (Amgen, Inc., Newbury Park, Calif.); REBETRON® (Schering Plough, Interferon-alpha 2B Ribavirin); pegylated interferon alpha (Reddy, K. R. et al., "Efficacy and Safety of Pegylated (40-kd) Interferon alpha-2a Compared with Interferon alpha-2a in Noncirrhotic Patients with Chronic Hepatitis C," *Hepatology*, 33, 433-438 (2001); consensus interferon (INFERGEN®) (Kao, J. H., et al., "Efficacy of Consensus Interferon in the Treatment of Chronic Hepatitis," *J. Gastroenterol. Hepatol.*, 15, 14184423 (2000); lymphoblastoid or "natural" interferon; interferon tau (Clayette, P. et al., "IFN-tau, A New Interferon Type I with Antiretroviral activity" *Pathol. Biol.* (Paris) 47, 553-559 (1999); interleukin-2 (Davis, G. L. et al., "Future Options for the Management of Hepatitis C." *Seminars in Liver Disease*, 19, 103-112 (1999); Interleukin-6 (Davis et al., "Future Options for the Management of Hepatitis C," *Seminars in Liver Disease*, 19, 103-112 (1999); interleukin-12 (Davis, G. L. et al., "Future Options for the Management of Hepatitis C." *Seminars in Liver Disease*, 19, 103-112 (1999); and compounds that enhance the development of type 1 helper T cell response (Davis et al., "Future Options for the Management of Hepatitis C," *Seminars in Liver Disease*, 19, 103-112 (1999)). Also included are compounds that stimulate the synthesis of interferon in cells (Tazulakhova, E. B. et al., "Russian Experience in Screening, analysis, and Clinical Application of Novel Interferon Inducers" *J. Interferon Cytokine Res.*, 21 65-73) including, but are not limited to, double stranded RNA, alone or in combination with tobramycin, and Imiquimod (3M Pharmaceuticals; Sander, D. N. "Immunomodulatory and Pharmacologic Properties of Imiquimod," *J. Am. Acad. Dermatol.*, 43 S6-11 (2000). See also, WO 02/18369, particularly page 272, line 15 to page 273, line 8, this disclosure being specifically incorporated herein by reference.

As is recognized by skilled practitioners, VX-950 is preferably administered orally. Interferon is not typically administered orally, although orally administered forms are in development. Nevertheless, nothing herein limits the methods or combinations of this invention to any specific dosage forms or regime. Thus, each component of a combination according to this invention may be administered separately, together, or in any combination thereof. As recognized by skilled practitioners, dosages of interferon are typically measured in IU (e.g., about 4 million IU to about 12 million IU). Interferon may also be dosed by micrograms. For example, a standard dose of Peg-Intron is 1.0-1.5 µg/kg/wk and of Pegasys is 180 µg/wk.

Ribavirin is typically administered orally, and tablet forms of ribavirin are currently commercially available. General standard, daily dose of ribavirin tablets (e.g., about 200 mg tablets) is about 800 mg to about 1200 mg. Nevertheless, nothing herein limits the methods or combinations of this invention to any specific dosage forms or regime. Typically, ribavirin can be dosed according to the dosage regimens described in its commercial product labels. A skilled practitioner would recognize that the dosage range of ribavirin can vary depending on body weight. A skilled practitioner would also recognize that the dosage can also be reduced to alleviate side effects.

In some aspects, the method includes the administration of agents over two phases, an initial phase and a secondary phase. For instance the initial phase can be a period of less than about 12 or 24 weeks and the secondary phase can be greater or equal to about 12 weeks, e.g., the secondary phase can be between about 12-36 weeks. In certain embodiments, the secondary phase is 12 weeks. In still other embodiments, the secondary phase is 36 weeks. In certain embodiments, the sum of the initial and secondary phase is about 24 to 48 weeks (such as 24, 36, or 48 weeks). In some embodiments, the initial and secondary phases can be identical in duration.

VX-950 may be administered in either the initial, secondary, or both phases. In some embodiments, VX-950 is administered only in the initial phase. When VX-950 is administered only in the initial phase, VX-950 may be administered alone or in combination with other agents and one or more agents are administered in the secondary phase. The other agents can be one or more anti-viral agents, one or more other agents described herein, or combinations thereof. In some embodiments, the specific agents administered in the initial and secondary phases are identical.

In some embodiments, the invention includes a therapeutic regimen comprising administering to a patient peginterferon and ribavirin with VX-950 in an initial phase and administering peginterferon and ribavirin over a secondary phase, wherein the secondary phase occurs after the initial phase, and wherein VX-950 is administered in an amount of 1125 mg twice per day, peginterferon is administered once per week and ribavirin is administered once per day.

In some embodiments, the invention includes a therapeutic regimen comprising administering to a patient peginterferon and ribavirin with VX-950 in an initial phase and administering peginterferon and ribavirin over a secondary phase, wherein the secondary phase occurs after the initial phase and VX-950 is administered in an amount of 1125 mg twice per day, peginterferon is administered once per week and ribavirin is administered once per day.

In some embodiments, the invention includes a therapeutic regimen comprising administering to a patient peginterferon and ribavirin with VX-950 in an initial phase and administering peginterferon and ribavirin over a secondary phase, wherein the secondary phase occurs after the initial phase and VX-950 is administered in an amount of 750 mg 3 times per day, peginterferon is administered in an amount of 180 micrograms per week and ribavirin is administered in an amount of 1000 to 1200 mg per day. In a specific embodiment, the peginterferon administered in the initial phase and in the secondary phase is peginterferon alfa 2a. In another specific embodiment, VX-950 is administered every 8 hours. In yet another specific embodiment, the peginterferon administered in the initial phase and in the secondary phase is peginterferon alfa 2b and VX-950 is administered every 8 hours.

In some embodiments, the invention includes a therapeutic regimen comprising administering to a patient peginterferon and ribavirin with VX-950 in an initial phase and administering peginterferon and ribavirin over a secondary phase, wherein the secondary phase occurs after the initial phase and VX-950 is administered in an amount of 750 mg 3 times per day, peginterferon is administered in an amount of 1.5 micrograms per kilogram per week and ribavirin is administered in an amount of 800 to 1200 mg per day. In a specific embodiment, the peginterferon administered in the initial phase and in the secondary phase is peginterferon alfa 2b. In another specific embodiment, VX-950 is administered every 8 hours. In yet another specific embodiment, the peginterferon administered in the initial phase and in the secondary phase is peginterferon alfa 2b and VX-950 is administered every 8 hours.

In some embodiments, the invention includes a therapeutic regimen comprising administering to a patient peginterferon and ribavirin with VX-950 in an initial phase and administering peginterferon and ribavirin over a secondary phase, wherein the secondary phase occurs after the initial phase, and wherein VX-950 is administered in an amount of 1125 mg twice per day, peginterferon is administered in an amount of 180 micrograms per week and ribavirin is administered in an amount of 1000 to 1200 mg per day. In a specific embodiment, the peginterferon administered in the initial phase and in the secondary phase is peginterferon alfa 2a. In another specific embodiment, VX-950 is administered every 12 hours. In yet another specific embodiment, the peginterferon administered in the initial phase and in the secondary phase is peginterferon alfa 2a and VX-950 is administered every 12 hours.

In some embodiments, the invention includes a therapeutic regimen comprising administering to a patient peginterferon and ribavirin with VX-950 in an initial phase and administering peginterferon and ribavirin over a secondary phase, wherein the secondary phase occurs after the initial phase, and wherein VX-950 is administered in an amount of 1125 mg twice per days, peginterferon is administered in an amount of 1.5 micrograms per kilogram per week and ribavirin is administered in an amount of 800 to 1200 mg per day. In a specific embodiment, the peginterferon administered in the initial phase and in the secondary phase is peginterferon alfa 2b. In another specific embodiment, VX-950 is administered every 12 hours. In yet another specific embodiment, the peginterferon administered in the initial phase and in the secondary phase is peginterferon alfa 2b and VX-950 is administered every 12 hours.

In some of the foregoing embodiments, at least 65% of patients have undetectable HCV RNA levels at week 4. In some embodiments, at least 75% of patients have undetectable HCV RNA levels at week 4. In some embodiments, at least 80% of patients have undetectable HCV RNA levels at week 4. In some embodiments, at least 85% of patients have undetectable HCV RNA levels at week 4.

In some of the foregoing embodiments, at least 80% of patients have undetectable HCV RNA levels at week 12. In some embodiments, at least 84% of patients have undetectable HCV RNA levels at week 12. In some embodiments, at least 85% of patients have undetectable HCV RNA levels at week 12. In some embodiments, at least 90% of patients have undetectable HCV RNA levels at week 12. In some embodiments, at least 93% of patients have undetectable HCV RNA levels at week 12.

In some embodiments, the method includes the administration of VX-950 for two weeks (initial phase) followed by 22 weeks of administration of a combination of Peginterferon alfa-2a and ribavirin (secondary phase). In other embodiments, the method includes the administration of VX-950 for two weeks (initial phase) followed by 46 weeks of administration of a combination of peginterferon and ribavirin (secondary phase).

In still other embodiments, the method includes the administration of VX-950 for two weeks in combination with peginterferon (initial phase) followed by 22 weeks of administration of a combination of peginterferon and ribavirin (secondary phase). In other embodiments, the method includes the administration of VX-950 for two weeks in combination with peginterferon (initial phase) followed by 46 weeks of administration of a combination of peginterferon and ribavirin (secondary phase).

In still other embodiments, the method includes the administration of VX-950 for two weeks in combination with peginterferon and ribavirin (initial phase) followed by 22 weeks of administration of a combination of peginterferon and ribavirin (secondary phase). In other embodiments, the method includes the administration of VX-950 for two weeks in combination with peginterferon and ribavirin (initial phase) followed by 46 weeks of administration of a combination of peginterferon and ribavirin (secondary phase).

In some embodiments, the method includes the administration of VX-950 for four weeks (initial phase) followed by 20 weeks of administration of a combination of peginterferon and ribavirin (secondary phase). In other embodiments, the method includes the administration of VX-950 for four weeks (initial phase) followed by 44 weeks of administration of a combination of peginterferon and ribavirin (secondary phase).

In still further embodiments, the method includes the administration of VX-950 for four weeks in combination with peginterferon (initial phase) followed by 20 weeks of administration of a combination of peginterferon and ribavirin (secondary phase). In other embodiments, the method includes the administration of VX-950 for four weeks in combination with peginterferon (initial phase) followed by 44 weeks of administration of a combination of peginterferon and ribavirin (secondary phase).

In still other embodiments, the method includes the administration of VX-950 for four weeks in combination with peginterferon and ribavirin (initial phase) followed by 20 weeks of administration of a combination of peginterferon and ribavirin (secondary phase). In other embodiments, the method includes the administration of VX-950 for four weeks in combination with peginterferon and ribavirin (initial phase) followed by 44 weeks of administration of a combination of peginterferon and ribavirin (secondary phase).

In some embodiments, any of the initial phases described above can be conducted for about 12 weeks and the secondary phases can be conducted for about 12 weeks. Alternatively, the initial phase can be conducted for about 12 weeks and the secondary phase can be conducted for about 24 weeks. In still other aspects, the initial phase can be conducted for about 12 weeks and the secondary phase can be conducted for about 36 weeks.

In some embodiments, any of the initial phases described above can be conducted for about 8 weeks and the secondary phases can be conducted for about 16 weeks. Alternatively, the initial phase can be conducted for about 8 weeks and the secondary phase can be conducted for about 28 weeks. In still other aspects, the initial phase can be conducted for about 8 weeks and the secondary phase can be conducted for about 40 weeks.

In some embodiments, the method includes administering VX-950 in combination with peginterferon for less than 48 weeks. For instance, the method includes administering VX-950 in combination with peginterferon for less than 24 weeks.

In some embodiments, the method includes administering VX-950 in combination with peginterferon and ribavirin for less than 48 weeks. For instance, the method includes administering VX-950 in combination with peginterferon and ribavirin for less than 24 weeks.

In one embodiment, a method of this invention comprises administering VX-950 for about 2 weeks (or 2 weeks) followed by administering peginterferon and ribavirin for about 22 weeks (or 22 weeks) or about 46 weeks (or 46 weeks).

Modeling data also indicate that VX-950 resistant variants, such as V36A/M, T54A, R155K/T, A156S A156V/T, V36A/M-R155K/T, and V36A/M-A156V/T, may be eradicated mainly by administering peginterferon and ribavirin for about 10-24 weeks (or 8-26 weeks) following VX-950 treatment. Certain of these regimens represent a reduction in treatment in the current standard of care treatment regimen lasting 24-48 weeks.

In some embodiments, the method of this invention is able to achieve week 4 RVR and week 12 undetectable status.

The viral relapse after 8 to 12 weeks of treatment of VX-950 was associated with VX-950-resistant variants and the relapse rates with 24- or 48-week of treatment were essentially the same, particularly in subjects showing a good initial response to the treatment.

The treatment with VX-950, peginterferon, and ribavirin for 12 weeks, and possibly as little as 8 weeks, appeared to be sufficient to clear wild-type virus.

Accordingly, this invention also provides methods for administering VX-950 in combination with an interferon. In certain embodiments, the interferon is administered for about 10 weeks (or 10 weeks), about 12 weeks (or 12 weeks), about 14 weeks (or 14 weeks). Ribavirin is also optionally administered for all or part of the regimen, including but not limited to, the entire regimen.

In one embodiment, a method of this invention comprises administering a combination of VX-950 and peginterferon for about 12 weeks (or 12 weeks).

In one embodiment, a method of this invention comprises administering a combination of VX-950 and peginterferon for about 12±4 weeks (e,g., 8, 12, or 16 weeks).

In one embodiment, a method of this invention comprises administering a combination of VX-950 and peginterferon for about 24 weeks (or 24 weeks).

In one embodiment, a method of this invention comprises administering a combination of VX-950 and peginterferon for about 24±4 weeks (e.g., 20, 24, or 28 weeks).

For the avoidance of doubt, it should be understood that this invention includes, but is not limited to, a regimen involving administering VX-950 and an interferon for about 8 weeks (or 8 weeks) followed by administering interferon for about 16 weeks (or 16 weeks) for a total treatment regimen of about 24 weeks (or 24 weeks). Also provided is a regimen involving administering VX-950 and an interferon for about 12 weeks (or 12 weeks) followed by administering interferon for about 12 weeks (or 12 weeks) for a total treatment regimen of about 24 weeks (or 24 weeks). Such regimens optionally provide administration of ribavirin for all or part of the regimen, including but not limited to, the entire regimen of about 24 weeks (or 24 weeks).

In one embodiment, a method of this invention comprises administering a combination of VX-950, peginterferon, and ribavirin for about 12 weeks (or 12 weeks).

In one embodiment, a method of this invention comprises administering a combination of VX-950, peginterferon, and ribavirin for about 12 weeks (or 12 weeks) followed by administering peginterferon and ribavirin for about 12 weeks (or 12 weeks).

In one embodiment, a method of this invention comprises administering a combination of VX-950, peginterferon, and ribavirin for about 12 weeks (or 12 weeks) followed by administering peginterferon and ribavirin for about 36 weeks (or 36 weeks).

In one embodiment, a method of this invention comprises administering a combination of VX-950, peginterferon, and ribavirin for about 24 weeks (or 24 weeks) followed by administering PEGIFN and ribavirin for about 24 weeks (or 24 weeks).

In some embodiments, the method includes providing a loading dose of VX-950 (1250 mg) followed by 750 mg q8h VX-950 plus a combination of peginterferon and ribavirin.

A cytochrome P450 monooxygenase ("CYP") inhibitor used in connection with this invention is expected to inhibit metabolism of VX-950. Therefore, the cytochrome P450 monooxygenase inhibitor would be in an amount effective to inhibit metabolism of VX-950. Accordingly, the CYP inhibitor is administered in an amount such that the bioavailability of or exposure to VX-950 is increased in comparison to VX-950 in the absence of the CYP inhibitor. CYP inhibitors include, but are not limited to, ritonavir (WO 94/14436), ketoconazole, troleandomycin, 4-methylpyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methylpyrazole, cyclosporin, and clomethiazole.

Methods for measuring the ability of a compound to inhibit cytochrome P50 monooxygenase activity are known (see, U.S. Pat. No. 6,037,157, and Yun et al., *Drug Metabolism & Disposition*, 21, 403-407 (1993)). Methods for evaluating the influence of co-administration of VX-950 and a CYP inhibitor in a subject are also known (US 2004/0028755). Any such methods could be used in connection with this invention to determine the pharmacokinetic impact of a combination.

One embodiment of this invention provides a method for administering an inhibitor of CYP3A4 and VX-950.

The methods herein may involve administration or co-administration of a) combinations of VX-950 and another agent; or b) VX-950 in more than one dosage form. Co-administration includes administering each inhibitor in the same dosage form or in different dosage forms. When administered in different dosage forms, the inhibitors may be administered at different times, including about simultaneously or in any time period around administration of the other dosage forms. Separate dosage forms may be administered in any order. That is, any dosage forms may be administered prior to, together with, or following the other dosage forms.

VX-950, and any additional agent, may be formulated in separate dosage forms. Alternatively, to decrease the number of dosage forms administered to a patient, VX-950, and any additional agent, may be formulated together in any combination. Any separate dosage forms may be administered at the same time or different times. It should be understood that dosage forms should be administered within a time period such that the biological effects were advantageous.

According to the regimens and dosage forms of this invention, VX-950 is present in an amount effective to decrease the viral load in a sample or in a patient, wherein said virus encodes a NS3/4A serine protease necessary for the viral life cycle (or in an amount effective to carry out a method of this invention), and a pharmaceutically acceptable carrier. Alternatively, a composition of this invention comprises an additional agent as described herein. Each component may be present in individual compositions, combination compositions, or in a single composition.

If pharmaceutically acceptable salts of compounds are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentane-propionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glutamine, and salts with amino acids such as arginine, lysine, and so forth.

Also, the basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, particularly a human being.

Such pharmaceutical compositions of the present invention (as well as compositions for use in methods, combinations, kits, and packs of this inventions) may be administered orally, parenterally, sublingually, by inhalation spray, topically, rectally, nasally, buccally, vaginally or via an implanted reservoir. The term "parenteral" as used herein includes subcutaneous, intravenous, intramuscular, intra-articular, intrasynovial, intrasternal, intrathecal, intrahepatic, intralesional and intracranial injection or infusion techniques. Preferably, the compositions are administered orally or intravenously. More preferably, the compositions are administered orally.

Sterile injectable forms of the compositions of and according to this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In compositions of this invention comprising VX-950 and an additional agent, VX-950 and the additional agent should be present at dosage levels of between about 10 to 100%, and more preferably between about 10 to 80% of the dosage normally administered in a monotherapy regimen.

The pharmaceutical compositions of this invention may be orally administered in any orally acceptable dosage form including, but not limited to, capsules, tablets, pills, powders, granules, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. Acceptable liquid dosage forms include emulsions, solutions, suspensions, syrups, and elixirs.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

As is recognized in the art, pharmaceutical compositions may also be administered in the form of liposomes.

Applicants have demonstrated that VX-950 is orally bioavailable. Accordingly, preferred pharmaceutical compositions of this invention are formulated for oral administration.

For the CYP inhibitor, the dosage levels of between about 0.001 to about 200 mg/kg body weight per day, would be typical. More typical would be dosage levels of between about 0.1 to about 50 mg/kg or about 1.1 to about 25 mg/kg per day.

For preferred dosage forms of ritonavir, see U.S. Pat. No. 6,037,157, and the documents cited therein: U.S. Pat. No. 5,484,801, U.S. patent application Ser. No. 08/402,690, and PCT Publications Nos. WO 95/07696 and WO 95/09614.

Administrations in connection with this invention can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

It should also be understood that a specific dosage and treatment regimen for any particular patient will depend upon a variety of factors, including the activity of the specific compound employed, the age, body weight, general health, sex, diet, time of administration, rate of excretion, drug combination, the judgment of the treating physician and the severity of the particular disease being treated, prior treatment history, co-morbidities or concomitant medications, baseline viral load, race, duration of diseases, status of liver function and degree of liver fibrosis/cirrhosis, and the goal of therapy (eliminating circulating virus per-transplant or viral eradication). The amount of active ingredients will also depend upon the particular described compound and the presence or absence and the nature of the additional anti-viral agent in the composition.

According to another embodiment, the invention provides a method for treating a patient infected with a virus characterized by a virally encoded NS3/4A serine protease that is necessary for the life cycle of the virus by administering to said patient a pharmaceutically acceptable composition of this invention. Preferably, the methods of this invention are used to treat a patient suffering from a HCV infection. Such treatment may completely eradicate the viral infection or reduce the severity thereof. Preferably, the patient is a mammal. More preferably, the patient is a human being.

The dosages herein are preferably for use in vivo. Nevertheless, this is not intended as a limitation to using of these amounts of VX-950 for any purpose. In yet another embodiment the present invention provides a method of pre-treating a biological substance intended for administration to a patient comprising the step of contacting said biological substance with a pharmaceutically acceptable composition comprising a compound of this invention. Such biological substances include, but are not limited to, blood and components thereof such as plasma, platelets, subpopulations of blood cells and the like; organs such as kidney, liver, heart, lung, etc; sperm and ova; bone marrow and components thereof, and other fluids to be infused into a patient such as saline, dextrose, etc.

This invention also provides a process for preparing a composition comprising VX-950, or a pharmaceutically acceptable salt thereof, and a pharmaceutically acceptable carrier, adjuvant, or vehicle comprising the step of combining the VX-950, or the pharmaceutically acceptable salt thereof, and the pharmaceutically acceptable carrier, adjuvant, or vehicle, wherein the dosage of VX-950 in the composition is in accordance with any embodiment of this invention. An alternative embodiment of this invention provides a process wherein the composition comprises one or more additional agent as described herein.

This invention also provides a therapeutic regimen comprising VX-950, or a pharmaceutically acceptable salt thereof, at the dosages disclosed herein. In an alternative embodiment of this invention, the therapeutic regimen further comprises one or more of additional agent as described herein.

Pharmaceutical compositions may also be prescribed to the patient in "patient packs" containing the whole course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions.

It will be understood that the administration of the combination of the invention by means of a single patient pack, or patient packs of each formulation, containing within a package insert instructing the patient to the correct use of the invention is a desirable additional feature of this invention.

According to a further aspect of the invention is a pack including VX-950 (in dosages according to this invention) and an information insert containing directions on the use of the combination of the invention. Any composition, dosage form, therapeutic regimen or other embodiment of this invention may be presented in a pharmaceutical pack. In an alternative embodiment of this invention, the pharmaceutical pack further comprises one or more of additional agent as described herein. The additional agent or agents may be provided in the same pack or in separate packs.

Another aspect of this involves a packaged kit for a patient to use in the treatment of HCV infection or in the prevention of HCV infection (or for use in another method of this invention), comprising: a single or a plurality of pharmaceutical formulation of each pharmaceutical component; a container housing the pharmaceutical formulation(s) during storage and prior to administration; and instructions for carrying out drug administration in a manner effective to treat or prevent HCV infection.

Accordingly, this invention provides kits for the simultaneous or sequential administration of a dose of VX-950 (and optionally an additional agent). Typically, such a kit will comprise, e.g. a composition of each compound and optional additional agent(s) in a pharmaceutically acceptable carrier (and in one or in a plurality of pharmaceutical formulations) and written instructions for the simultaneous or sequential administration.

In another embodiment, a packaged kit is provided that contains one or more dosage forms for self administration; a container means, preferably sealed, for housing the dosage forms during storage and prior to use; and instructions for a patient to carry out drug administration. The instructions will typically be written instructions on a package insert, a label, and/or on other components of the kit, and the dosage form or forms are as described herein. Each dosage form may be individually housed, as in a sheet of a metal foil-plastic laminate with each dosage form isolated from the others in individual cells or bubbles, or the dosage forms may be housed in a single container, as in a plastic bottle. The present kits will also typically include means for packaging the individual kit components, i.e., the dosage forms, the container means, and the written instructions for use. Such packaging means may take the form of a cardboard or paper box, a plastic or foil pouch, etc.

A kit according to this invention could embody any aspect of this invention such as any composition, dosage form, therapeutic regimen, or pharmaceutical pack.

The packs and kits according to this invention optionally comprise a plurality of compositions or dosage forms. Accordingly, included within this invention would be packs and kits containing one composition or more than one composition.

Although certain exemplary embodiments are depicted and described below, it will be appreciated that compounds of this invention can be prepared according to the methods described generally above using appropriate starting materials generally available to one of ordinary skill in the art.

All cited documents are incorporated herein by reference.

In order that this invention be more fully understood, the following preparative and testing examples are set forth. These examples are for the purpose of illustration only and are not to be construed as limiting the scope of the invention in any way.

VX-950 may be prepared in general by methods known to those skilled in the art (see, e.g., WO 02/18369). Any suitable formulations known in the art can be used in the invention. For example, formulations described in WO 2005/123075, WO 2007/109604, WO 2007/109605 and WO 2008/080167 can be employed in the invention. A specific formulation that can be used in the invention is exemplified in Example 6. Other specific examples include:

| | | |
|---|---|---|
| VX-950 | 49.5 wt % | |
| HPMC 40 cp | 49.5 wt % | |
| SLS | 1 wt % | |
| VX-950 | 49.5 wt % | |
| HPC | 49.5 wt % | |
| SLS | 1 wt % | |
| VX-950 | 49.5 wt % | |
| PVP K30 | 49.5 wt % | |
| SLS | 1 wt % | |
| VX-950 Solid Dispersion | | |
| % (w/w) | Ingredient | |
| 49.5 | VX-950 | Spray-dried from a MeCl$_2$ solution |
| 49.5 | PVP K29/32 | |
| 1 | SLS | | wherein HPMC (Hydroxypropyl Methylcellulose, 60SH 50cP, Biddle Sawyer or Shin-Etsu Metolose, HPMC60SH50), (Hypromellose Acetate Succinate, HG grade, Shin-Etsu Chemical Co.), HPC (hydroxypropyl cellulose), PVP (polyvinylpyrrolidone) and SLS (Sodium Lauryl Sulfate) are as described in WO 2005/123075. In certain embodiments, the solid dispersion shown above can be suspended in a 1% HPMC, 0.002% simethicone solution (1 wt % HPMC, 0.002 wt % simethicone and 99 wt % water). Additional examples include 1:1 VX950: PVPK30, 1 wt % SLS (Refreshed Tox.); Niro-49 wt % HPMCAS/1 wt % SLS/1 wt % SDBS/49% VX-950; 40.5 wt % PVP-VA/10 wt % ETPGS/49.5 wt % VX-950; 40.5 wt % HPMC/10 wt % ETPGS/49.5 wt % VX-950; 49 wt % VX950, 49 wt % HPMCAS, 1 wt % SLS, 1 wt % SDBS; and 49 wt % VX950, 16 wt % HPPh, 33 wt % HPC, 1 wt % SLS, wt % SDBS, wherein PVPK30 (Polyvinyl Pyrrolidone K30), SUBS (sodium dodecyl benzene sulfonate), HPMCAS (Hydroxypropyl Methylcellulose Acetate Succinate), Vitamin ETPGS, PVP (polyvinylpyrrolidone) and SLS (Sodium Lauryl Sulfate), and details of the preparation of these formulations can be found in WO 2005/123075. Additional examples include those described in WO 2007/109604:

a solid dispersion comprising 55 wt % VX-950, 24.4 wt % HPMCAS-HG (Hydroxypropyl Methylcellulose Acetate Succinate, JPE, Biddle Sawyer or Shin-Etsu HPMCAS-HG grade), 19.6 wt % HPMC-60SH (Hydroxypropyl Methylcellulose, 60SH 50cP, Biddle Sawyer or Shin-Etsu Metolose, HPMC60SH50), and 1 wt % Sodium Lauryl Sulfate (SLS);

a solid dispersion comprising 55 wt % VX-950, 14.7 wt % HPMCAS-HG (Hydroxypropyl Methylcellulose Acetate Succinate, JPE, Biddle Sawyer or Shin-Etsu HPMCAS-HG grade), 29.3 wt % HPMC-60SH (Hydroxypropyl Methylcellulose, 60SH 50cP, Biddle Sawyer or Shin-Etsu Metolose, HPMC60SH50), and 1 wt % Sodium Lauryl Sulfate (SLS);

a solid dispersion comprising 60 wt % VX-950, 24.4 wt % HPMCAS-HG (Hydroxypropyl Methylcellulose Acetate Succinate, JPE, Biddle Sawyer or Shin-Etsu HPMCAS-HG grade), 14.6 wt % HPMC-60SH (Hydroxypropyl Methylcellulose, 60SH 50cP, Biddle Sawyer or Shin-Etsu Metolose, HPMC60SH50), and 1 wt % Sodium Lauryl Sulfate (SLS);

a solid dispersion comprising 65 wt % VX-950, 17 wt % HPMCAS-HG (Hydroxypropyl Methylcellulose Acetate Succinate, JPE, Biddle Sawyer or Shin-Etsu HPMCAS-HG grade), 17 wt % HPMC-60SH (Hydroxypropyl Methylcellulose, 60SH 50cP, Biddle Sawyer or Shin-Etsu Metolose, HPMC60SH50), and 1 wt % Sodium Lauryl Sulfate (SLS);

a solid dispersion comprising 70 wt % VX-950, 9.7 wt % HPMCAS-HG (Hydroxypropyl Methylcellulose Acetate Succinate, JPE, Biddle Sawyer or Shin-Etsu HPMCAS-HG grade), 19.3 wt % HPMC-60SH (Hydroxypropyl Methylcellulose, 60SH 50cP, Biddle Sawyer or Shin-Etsu Metolose, HPMC60SH50), and 1 wt % Sodium Lauryl Sulfate (SLS);

a solid dispersion comprising 60 wt % VX-950, 39 wt % HPMCAS-HG (Hydroxypropyl Methylcellulose Acetate Succinate, JPE, Biddle Sawyer or Shin-Etsu HPMCAS-HG grade), and 1 wt % Sodium Lauryl Sulfate (SLS);

a solid dispersion comprising 49.5 wt % VX-950, 24.5 wt % HPMCAS-HG (Hydroxypropyl Methylcellulose Acetate Succinate, JPE, Biddle Sawyer or Shin-Etsu HPMCAS-HG grade), 24.5 wt % HPMC-60SH (Hydroxypropyl Methylcellulose, GOSH 50cP, Biddle Sawyer or Shin-Etsu Metolose, HPMC60SH50), and 1 wt % Sodium Lauryl Sulfate (SLS);

a solid dispersion comprising 83 wt % VX-950, 8 wt % HPMCAS-HG (Hydroxypropyl Methylcellulose Acetate Succinate, JPE, Biddle Sawyer or Shin-Etsu HPMCAS-HG grade), 8 wt % HPMC-60SH (Hydroxypropyl Methylcellulose, 60SH 50cP, Biddle Sawyer or Shin-Etsu Metolose, HPMC60SH50), and 1 wt % Sodium Lauryl Sulfate (SLS);

a solid dispersion comprising 49.5 wt % VX-950, 24.5 wt % HPMCAS-HG (Hydroxypropyl Methylcellulose Acetate Succinate, JPE, Biddle Sawyer or Shin-Etsu HPMCAS-HG grade), 24.5 wt % HPMC-60SH (Hydroxypropyl Methylcellulose, 60SH 50cP, Biddle Sawyer or Shin-Etsu Metolose, HPMC60SH50), and 1 wt % Sodium Lauryl Sulfate (SLS);

a solid dispersion comprising 70 wt % VX-950, 14.5 wt % HPMCAS-HG (Hydroxypropyl Methylcellulose Acetate Succinate, JPE, Biddle Sawyer or Shin-Etsu HPMCAS-HG grade), 14.5 wt % HPMC-60SH (Hydroxypropyl Methylcellulose, 60SH 50cP, Biddle Sawyer or Shin-Etsu Metolose, HPMC60SH50), and 1 wt % Sodium Lauryl Sulfate (SLS);

a solid dispersion comprising 65 wt % VX-950, 14.6 wt % HPMCAS-HG (Hydroxypropyl Methylcellulose Acetate Succinate, JPE, Biddle Sawyer or Shin-Etsu HPMCAS-HG grade), 19.4 wt % HPMC-60SH (Hydroxypropyl Methylcellulose, 60SH 50cP, Biddle Sawyer or Shin-Etsu Metolose, HPMC60SH50), and 1 wt % Sodium Lauryl Sulfate (SLS);

a solid dispersion comprising 65 wt % VX-950, 9.7 wt % HPMCAS-HG (Hydroxypropyl Methylcellulose Acetate Succinate, JPE, Biddle Sawyer or Shin-Etsu HPMCAS-HG grade), 24.3 wt % HPMC-60SH (Hydroxypropyl Methylcellulose, 60SH 50cP, Biddle Sawyer or Shin-Etsu Metolose, HPMC60SH50), and 1 wt % Sodium Lauryl Sulfate (SLS);

a solid dispersion comprising 60 wt % VX-950, 19.5 wt % HPMCAS-HG (Hydroxypropyl Methylcellulose Acetate Succinate, JPE, Biddle Sawyer or Shin-Etsu HPMCAS-HG grade), 19.5 wt % HPMC-60SH (Hydroxypropyl Methylcellulose, 60SH 50cP, Biddle Sawyer or Shin-Etsu Metolose, HPMC60SH50), and 1 wt % Sodium Lauryl Sulfate (SLS);

a solid dispersion comprising 60 wt % VX-950, 14.6 wt % HPMCAS-HG (Hydroxypropyl Methylcellulose Acetate Succinate, JPE, Biddle Sawyer or Shin-Etsu HPMCAS-HG grade), 24.4 wt % HPMC-60SH (Hydroxypropyl Methylcellulose, 60SH 50cP, Biddle Sawyer or Shin-Etsu Metolose, HPMC60SH50), and 1 wt % Sodium Lauryl Sulfate (SLS);

a solid dispersion comprising 70 wt % VX-950, 9.7 wt % HPMCAS-HG (Hydroxypropyl Methylcellulose Acetate Succinate, JPE, Biddle Sawyer or Shin-Etsu HPMCAS-HG grade), 19.3 wt % HPMC-60SH (Hydroxypropyl Methylcellulose, 60SH 50cP, Biddle Sawyer or Shin-Etsu Metolose, HPMC60SH50), and 1 wt % Sodium Lauryl Sulfate (SLS);

a solid dispersion comprising 49.5 wt % VX-950, 24.5 wt % HPMCAS-HG (Hydroxypropyl Methylcellulose Acetate Succinate, JPE, Biddle Sawyer or Shin-Etsu HPMCAS-HG grade), 24.5 wt % HPMC-60SH (Hydroxypropyl Methylcellulose, 60SH 50cP, Biddle Sawyer or Shin-Etsu Metolose, HPMC60SH50), and 1 wt % Sodium Lauryl Sulfate (SLS);

a solid dispersion comprising 83 wt % VX-950, 8 wt % HPMCAS-HG (Hydroxypropyl Methylcellulose Acetate Succinate, JPE, Biddle Sawyer or Shin-Etsu HPMCAS-HG grade), 8 wt % HPMC-60SH (Hydroxypropyl Methylcellulose, 60SH 50cP, Biddle Sawyer or Shin-Etsu Metolose, HPMC60SH50), and 1 wt % Sodium Lauryl Sulfate (SLS);

a solid dispersion comprising 49.5 wt % VX-950, 49.5 wt % HPMCAS-HG (Hydroxypropyl Methylcellulose Acetate Succinate, JPE, Biddle Sawyer or Shin-Etsu HPMCAS-HG grade), and 1 wt % Sodium Lauryl Sulfate (SLS);

a solid dispersion comprising 83 wt % VX-950, 16 wt % HPMCAS-HG (Hydroxypropyl Methylcellulose Acetate Succinate, JPE, Biddle Sawyer or Shin-Etsu HPMCAS-HG grade), and 1 wt % Sodium Lauryl Sulfate (SLS);

a solid dispersion comprising 82.44 wt % VX-950, 15.89 wt % HPMCAS-HG (Hydroxypropyl Methylcellulose Acetate Succinate, JPE, Biddle Sawyer or Shin-Etsu HPMCAS-HG grade), and 1.67 wt % Sodium Lauryl Sulfate (SLS);

a solid dispersion comprising 49.5 wt % VX-950, 24.75 wt % HPMCAS-HG (Hydroxypropyl Methylcellulose Acetate Succinate, JPE, Biddle Sawyer or Shin-Etsu HPMCAS-HG grade), 24.75 wt % HPMC-60SH (Hydroxypropyl Methylcellulose, 60SH 50cP, Biddle Sawyer or Shin-Etsu Metolose, HPMC60SH50), and 1 wt % Sodium Lauryl Sulfate (SLS).

a solid dispersion comprising 60 wt % VX-950, 24.6 wt % HPMCAS-HG (Hydroxypropyl Methylcellulose Acetate Succinate, JPE, Biddle Sawyer or Shin-Etsu HPMCAS-HG grade), 14.4 wt % HPMC-60SH (Hydroxypropyl Methylcellulose, 60SH 50cP, Biddle Sawyer or Shin-Etsu Metolose, HPMC60SH50), and 1 wt % Sodium Lauryl Sulfate (SLS);

a solid dispersion comprising 60 wt % VX-950, 39 wt % HPMCAS-HG (Hydroxypropyl Methylcellulose Acetate Succinate, JPE, Biddle Sawyer or Shin-Etsu HPMCAS-HG grade), and 1 wt % Sodium Lauryl Sulfate (SLS); and a solid dispersion comprising 49.5 wt % VX-950, 49.5 wt % HPMCAS-HG (Hydroxypropyl Methylcellulose Acetate Succinate, JPE, Biddle Sawyer or Shin-Etsu HPMCAS-HG grade), and 1 wt % Sodium Lauryl Sulfate (SLS).

Details of the preparation of these solid dispersions are described in WO 2007/109604. Additional specific examples include tablet formulations containing a spray dried dispersion of VX-950, which are described in WO 2007/109604:

| Component | mg per Tablet | Percent |
|---|---|---|
| Roller compaction blend | | |
| VX950 Spray Dried Dispersion1 | 505.1 | 74.9 |
| Pharmatose DCL 22 (Lactose, USP/NF, PhEur) | 37.5 | 5.6 |
| Ac-Di-Sol (cross carmellose sodium, NF, PhEur) | 24.0 | 3.6 |
| Extragranular addition | | 0.0 |
| Avicel pH 113 | 33.7 | 5.0 |
| Vitamin E TPGS (NF) | 24.0 | 3.6 |
| Ac-Di-Sol (cross carmellose sodium, NF, PhEur) | 16.0 | 2.4 |
| Cabosil M-5 (colloidal silicon dioxide, NF, PhEur) | 8.0 | 1.2 |
| Sodium Stearyl fumarate (NF, PhEur, JP) | 26.0 | 3.9 |
| Total Formulation weight | 674.3 | 100.0 |

Additional specific examples include tablet formulations described in WO2008/080167:

| VX950 SD Tableting Experiment Design (Potency: 250 mg VX950) | | |
|---|---|---|
| Trial # | Vit E type | Vit E type |
| A | VitE-TPGS (24 mg) | Granulated VitE on excipients |
| C | VitE-Acetate (48 mg) | Used as is |
| E | Vit E-TPGS(24 mg) | Vit E Spray Congealed |
| F | Vit E-TPGS (24 mg) | Granulated Vit E onto VX950 |

| Trial# A Formulation | | | |
|---|---|---|---|
| Item | Ingredients | Wt/Tablet (mg) | wt % |
| | Physical mixture | | |
| 1 | Solid Dispersion (73.55% VX950/26.45% HPMCAS) | 339.9 | 66.32 |
| 2 | PHARMATOSE ® DCL 22 (Lactose) | 37.5 | 7.32 |
| 3 | AC-DI-SOL ® (Cross carmellose sodium) | 24.0 | 4.68 |
| 4 | Sodium Stearyl Fumarate | 1.6 | 0.32 |
| 5 | SLS | 3.4 | 0.66 |
| 6 | AVICEL ® pH 113 (Microcrystalline cellulose) | 33.7 | 6.58 |
| 7 | Vitamin E TPGS (granulated on excipients) | 24.0 | 4.68 |
| 8 | AC-DI-SOL ® (Cross carmellose sodium) | 16.0 | 3.12 |
| 9 | Cabosil M-5 (Colloidal silicon dioxide) | 8.0 | 1.56 |
| 10 | Sodium Stearyl Fumarate | 24.4 | 4.76 |
| | Total | 512.5 | 100 |

Note:
VX 950 SD Lot 02
Potency: 250 mg VX950

| Trial# C Formulation | | | |
|---|---|---|---|
| Item | Ingredients | wt/Tablet (mg) | wt % |
| | Physical mixture | | |
| 1 | Solid Dispersion (73.55% VX950/26.45% HPMCAS) | 339.9 | 63.36 |
| 2 | PHARMATOSE ® DCL 22 (Lactose) | 37.5 | 6.99 |
| 3 | AC-DI-SOL ® (Cross carmellose sodium) | 24.0 | 4.47 |
| 4 | Sodium Stearyl Fumarate | 1.6 | 0.30 |
| 5 | SLS | 3.4 | 0.63 |
| 6 | AVICEL ® pH 113 (Microcrystalline cellulose) | 33.7 | 6.28 |
| 7 | Vitamin E-Acetate | 48.0 | 8.95 |
| 8 | AC-DI-SOL ® (Cross carmellose sodium) | 16.0 | 2.98 |
| 9 | Cabosil M-5 (Colloidal silicon dioxide) | 8.0 | 1.49 |
| 10 | Sodium Stearyl Fumarate | 24.4 | 4.54 |
| | Total | 536.5 | 100 |

| Trial# E Formulation | | | |
|---|---|---|---|
| Item | Ingredients | Wt/Tablet (mg) | wt % |
| | Physical mixture | | |
| 1 | Solid Dispersion (73.55% VX950/26.45% HPMCAS) | 339.9 | 66.32 |
| 2 | PHARMATOSE ® DCL 22 (Lactose) | 37.5 | 7.32 |
| 3 | AC-DI-SOL ® (Cross carmellose sodium) | 24.0 | 4.68 |
| 4 | Sodium Stearyl Fumarate | 1.6 | 0.32 |
| 5 | SLS | 3.4 | 0.66 |
| 6 | AVICEL ® pH 113 (Microcrystalline cellulose) | 33.7 | 6.58 |
| 7 | Vitamin E Spray Congealed | 24.0 | 4.68 |
| 8 | AC-DI-SOL ® (Cross carmellose sodium) | 16.0 | 3.12 |
| 9 | Cabosil M-5 (Colloidal silicon dioxide) | 8.0 | 1.56 |
| 10 | Sodium Stearyl Fumarate | 24.4 | 4.76 |
| | Total | 512.5 | 100 |

Note:
VX 950 SD Lot 02
Potency: 250 mg VX950

| Trial# F Formulation | | | |
|---|---|---|---|
| Item | Ingredients | Wt/Tablet (mg) | wt % |
| 1 | Solid Dispersion (73.55% VX950/26.45% HPMCAS) | 339.9 | 66.32 |
| 2 | Vitamin E granulated onto dispersion | 24.0 | 4.68 |
| 3 | PHARMATOSE ® DCL 22 (Lactose) | 37.5 | 7.32 |
| 4 | AC-DI-SOL ® (Cross carmellose sodium) | 24.0 | 4.68 |
| 5 | Sodium Stearyl Fumarate | 1.6 | 0.32 |
| 6 | SLS | 3.4 | 0.66 |
| 7 | AVICEL ® pH 113 (Microcrystalline cellulose) | 33.7 | 6.58 |
| 8 | AC-DI-SOL ® (Cross carmellose sodium) | 16.0 | 3.12 |

-continued

Trial# F Formulation

| Item | Ingredients | Wt/Tablet (mg) | wt % |
|---|---|---|---|
| 9 | Cabosil M-5 (Colloidal silicon dioxide) | 8.0 | 1.56 |
| 10 | Sodium Stearyl Fumarate | 24.4 | 4.76 |
|  | Total | 512.5 | 100 |

Note:
VX 950 SD Lot 02
Potency: 250 mg VX950

All cited documents are incorporated herein by reference.

In order that this invention be more fully understood, the following preparative and testing examples are set forth. These examples are for the purpose of illustration only and are not to be construed as limiting the scope of the invention in any way.

EXAMPLE 1

HCV Replicon Cell Assay Protocol

Cells containing hepatitis C virus (HCV) replicon were maintained in DMEM containing 10% fetal bovine serum (FBS), 0.25 mg per mL of G418, with appropriate supplements ("media A").

On day 1, a replicon cell monolayer was treated with a trypsin:EDTA mixture, removed, and then media A was diluted into a final concentration of 100,000 cells per mL. 10,000 cells in 100 μL were plated into each well of a 96-well tissue culture plate, and cultured overnight in a tissue culture incubator at 37° C.

On day 2, compound VX-950 in 100% DMSO were serially diluted into DMEM containing 2% FBS, 0.5% DMSO, with appropriate supplements ("media B") to obtained solutions containing VX-950 at different concentrations. The final concentration of DMSO was maintained at 0.5% throughout the dilution series.

Media A on the replicon cell monolayer was removed, and then media B containing various concentrations of VX-950 was added. Media B without any compound was added to other wells as control.

Cells were incubated with VX-950 solutions in media B or control for 48 hours in a tissue culture incubator at 37° C. At the end of the 48-hour incubation period, media B was removed, and the replicon cell monolayer was washed once with PBS and stored at −80° C. prior to RNA extraction.

The culture plates with treated replicon cell monolayers were thawed, and a fixed amount of another RNA virus, Bovine Viral Diarrhea Virus (BVDV), was added to the cells in each well. RNA extraction reagents (such as reagents from RNeasy kits) were added to the cells immediately to avoid degradation of RNA. Total RNA was extracted according the instruction of manufacturer with modification to improve extraction efficiency and consistency. Finally, total cellular RNA, including HCV replicon RNA, was eluted and stored at −80° C. until further processing.

A TAQMAN™ real-time RT-PCR quantification assay was set up with two sets of specific primers and probe. One was for HCV and the other was for BVDV. Total RNA extractant from treated HCV replicon cells was added to the PCR reaction for quantification of both HCV and BVDV RNA in the same PCR well. Experimental failure was flagged and rejected based on the level of BVDV RNA in each well. The level of HCV RNA in each well was calculated according to a standard curve run in the same PCR plate. The percentage of inhibition or decrease of HCV RNA level due to VX-950 treatment was calculated using the DMSO or VX-950-free control as 0% of inhibition. The $IC_{50}$ (concentration at which 50% inhibition of HCV RNA level is observed) was calculated from the titration curve of any VX-950 concentrations.

The results show that VX-950 had significant inhibitory activity in the replicon assay, with the $IC_{50}$ of about 240 ng/mL and $IC_{90}$ of about 476 ng/mL.

EXAMPLE 2

HCV Ki Assay Protocol

HPLC Microbore Method for Separation of 5AB Substrate and Products

Substrate used this study was:

$NH_2$-Glu-Asp-Val-Val-(alpha)Abu-Cys-Ser-Met-Ser-Tyr-COOH. SEQ ID NO:1

A stock solution of 20 mM 5AB was made in DMSO with 0.2M DTT and stored in aliquots at −20° C. A buffer of pH 7.8 was made to contain 50 mM HEPES, 100 mM NaCl, and 20% glycerol.

Assay solutions of 100 μL were prepared according to Table 1.

TABLE 1

|  | X1 (μL) | conc. in assay |
|---|---|---|
| Buffer | 86.5 | See above |
| 5 mM KK4A | 0.5 | 25 μM |
| 1M DTT | 0.5 | 5 mM |
| DMSO or VX-950 | 2.5 | 2.5% v/v |
| 50 μM tNS3 | 0.05 | 25 nM |
| 250 μM 5AB (initiate) | 20 | 25 μM |

The buffer, KK4A, DTT, and tNS3 were combined, and distributed 78 μL each into wells of a 96-well plate, followed by incubation at 30° C. for 5 to 10 minutes.

2.5 μL of appropriate concentration of VX-950 was dissolved in DMSO (DMSO only for control) and added to each well, followed by incubation at the room temperature for 15 minutes.

The reaction was initiated by addition of 20 μL of 250 μM 5AB substrate (25 μM concentration is equivalent to or slightly lower than the $K_m$ for 5AB). The resultant mixture was incubated at 30° C. for 20 minutes, before the reaction was terminated by the addition of 25 μL of 10% TFA and the mixture transferred (in 120 μL aliquots) to HPLC vials for analysis.

SMSY product was separated from the substrate and KK4A by the following method:

Instrumentation: Agilent 1100

Degasser G1322A

Binary pump G1312A

Autosampler G1313A

Column thermostated chamber G1316A

Diode array detector G1315A

Column:

Phenomenex Jupiter; 5 micron C18; 300 angstroms; 150×2 mm; P/O 00F-4053-B0

Column thermostat: 40 C

Injection volume: 100 μL

Solvent A=HPLC grade water+0.1% TFA

Solvent B=HPLC grade acetonitrile+0.1% TFA

TABLE 2

| Time (min) | % B | Flow (mL/min) | Max press. |
|---|---|---|---|
| 0 | 5 | 0.2 | 400 |
| 12 | 60 | 0.2 | 400 |
| 13 | 100 | 0.2 | 400 |
| 16 | 100 | 0.2 | 400 |
| 17 | 5 | 0.2 | 400 |

Stop time: 17 min
Post-run time: 10 min.

EXAMPLE 3

Tolerance and Pharmacokinetics Studies

VX-950 was examined in a randomized, double-blind, placebo-controlled single-dose escalation study. 25 healthy male volunteers were enrolled and each received multiple single doses of VX-950 (at least 7 days apart, 3 doses of VX-950 at increasing dose levels) and 1 dose of placebo.

Doses of 25 mg to 1250 mg were evaluated. A dose escalation scheme was used that combined dose doubling and modified Fibonacci to be aggressive in the lower dose range and conservative in the higher dose range.

The results showed that VX-950 was well tolerated at all dose levels. No serious adverse events were reported during the study, and there did not appear to be an increase in adverse events with increasing dose levels.

A pharmacokinetics analysis was performed using the statistical moment approach. Pharmacokinetic analysis showed that VX-950 was absorbed with a median $t_{max}$ of 3 hours. Less than 2% of VX-950 was eliminated unchanged in the urine, indicating that the drug is primarily eliminated via the metabolic route.

EXAMPLE 4

Infectious Virus Assay

VX-950 demonstrated an $IC_{50}$ of 196 ng/mL in the infectious virus assy.

EXAMPLE 5

Effects of VX-950 Treatment

VX-950 was examined in a randomized, placebo-controlled, multiple-dose, blinded, dose escalation study in 24 healthy subjects and 36 Hepatitis C positive subjects.

The 24 healthy subjects were divided into 3 panels of 8 subjects each. In each panel, 6 subjects received VX-950 and 2 subjects received placebo. Healthy subjects were dosed with VX-950 at 450 mg, 750 mg, or 1250 mg q8h for 5 consecutive days. The healthy subjects were between the ages of 18-65 years (inclusive) and were Hepatitis B, Hepatitis C, and HIV negative. The males had a body mass index of 18.5-29.0 kg/m² (inclusive). The females had a body mass index of 18.5-32.5 kg/m² (inclusive).

Hepatitis C (genotype 1) positive subjects were divided into 3 panels of 12 subjects each for receiving VX-950 at 450 mg q8h, 750 mg q8h, or 1250 mg q12h for 14 consecutive days. In each panel, 10 subjects received VX-950 and 2 subjects received placebo. In the 750 mg group, 2 subjects withdrew prior to dosing. All other 34 subjects completed the study.

The study showed that VX-950 was well tolerated at all dose levels and no serious adverse events were reported during the study; mild and moderate adverse events were reported. Among the HCV positive subjects receiving placebo, 450 mg q8h, 750 mg q8h, and 1250 mg q12h groups, 33.2%, 10%, 12.5%, and 30%, respectively, were treatment-naïve.

The HCV positive subjects were tested post-treatment to monitor HCV RNA levels' return to baseline.

TABLE 3

Subject Baseline Characteristics

| | | VX-950 dose | | |
|---|---|---|---|---|
| | Placebo (n = 6) | 450 mg q8h (n = 10) | 750 mg q8h (n = 8) | 1250 mg q12h (n = 10) |
| Sex, n (%) | | | | |
| Male | 3 (50.0) | 8 (80.0) | 3 (37.5) | 8 (80.0) |
| Female | 3 (50.0) | 2 (20.0) | 5 (62.5) | 2 (20.0) |
| Race, n (%) | | | | |
| Caucasian | 6 (100) | 10 (100) | 8 (100) | 10 (100) |
| Age, years | | | | |
| Median | 54.0 | 47.0 | 52.0 | 43.5 |
| Range | 31-64 | 33-64 | 46-64 | 25-62 |
| BMI, kg/m² | | | | |
| Median | 24.8 | 25.8 | 27.0 | 22.2 |
| Range | 21.0-29.0 | 22.6-28.4 | 21.1-29.4 | 21.2-24.3 |
| HCV RNA, $\log_{10}$ IU/mL | | | | |
| Mean ± SD | 6.28 ± 0.47 | 6.54 ± 0.50 | 6.18 ± 0.47 | 6.46 ± 0.41 |
| Approximate years HCV infection, mean ± SD | 7.3 ± 7.6 | 9.2 ± 11.5 | 7.2 ± 7.6 | 6.9 ± 6.7 |
| HCV subtype, n (%) | | | | |
| 1* | 1 (16.7) | 0 | 2 (25.0) | 1 (10.0) |
| 1a | 2 (33.3) | 3 (30.0) | 1 (12.5) | 5 (50.0) |
| 1b | 3 (50.0) | 7 (70.0) | 5 (62.5) | 4 (40.0) |

TABLE 3-continued

Subject Baseline Characteristics

| | | VX-950 dose | | |
|---|---|---|---|---|
| | Placebo (n = 6) | 450 mg q8h (n = 10) | 750 mg q8h (n = 8) | 1250 mg q12h (n = 10) |
| Prior HCV treatment n (%) | 4 (66.7) | 9 (90.0) | 7 (87.5) | 7 (70.0) |

*Samples from 4 patients were classified as genotype 1 because the assay could not determine whether they were genotype 1a or 1b.
Abbreviations:
BMI (body mass index);
HCV (hepatitis C virus);
q8h (every 8 hours);
q12h (every 12 hours);
SD (standard deviation).
HCV RNA change from baseline, study VX04-950-101

TABLE 4

Maximum changes in HCV RNA by category

| | | VX-950 dose | | |
|---|---|---|---|---|
| Change From Baseline in HCV RNA ($\log_{10}$ IU/mL) | Placebo (n = 6) | 450 mg q8h (n = 10) | 750 mg q8h (n = 8) | 1250 mg q12h (n = 10) |
| >−1 to <0 | 6 (100.0) | 0 | 0 | 0 |
| >−2 to ≤−1 | 0 | 0 | 0 | 0 |
| >−3 to ≤−2 | 0 | 1 (10.0) | 0 | 1 (10.0) |
| >−4 to ≤−3 | 0 | 7 (70.0) | 3 (37.5) | 9 (90.0) |
| >−5 to ≤−4 | 0 | 0 | 3 (37.5) | 0 |
| ≥−5 | 0 | 2 (20.0) | 2 (25.0) | 0 |

Values are n (%): q8h, every 8 hours; q12h, every 12 hours.

EXAMPLE 6

Formulation of VX-950

An oral dosage formulation was prepared as follows. VX-950 and povidone K29/32 were dissolved in methylene chloride, then sodium lauryl sulfate was added to and dispersed in the VX-950 solution to form a homogenous suspension. This suspension was spray-dried using an inlet temperature of 90° C. and an outlet temperature of 56° C., and the product was collected from the cyclone. The spray-dried dispersion was fluid-bed dried at 75° C. for 8 hours. The resultant powder was pre-measured into glass vials, and just prior to dosing was suspended in water (30 mL) for administration to the subjects. In connection with dosing, each vial was washed with 3 separate portions of water, with the total volume of water being 90 mL.

TABLE 5

VX-950 Solid Dispersion

| % (w/w) | Ingredient | |
|---|---|---|
| 49.5 | VX-950 | Spray-dried from $CH_2Cl_2$ |
| 49.5 | PVP K29/32 | |
| 1 | SLS | |

EXAMPLE 7

VX-950 Validation in Human Plasma

The assay for determined VX-950 concentration in human plasma was performed by methods well known in the art. See, e.g., Wasley, A. et al., *Semin. Liver Dis.*, 20:1-16, 2000; Alter, H. J. et al., *Semin. Liver Dis.*, 20: 17-35, 2000; Brown, R. S. Jr. et al., *Liver Transpl.*, 9: S10-S13, 2003; DeFrancesco, R. et al., *Nature,* 436(7053): 953-960, 2005; Bowen, D. G. et al., J. Hepatol., 42: 408-417, 2005; Hoofnagle, J. H., Hepatology, 36: S21-S29, 2002, Brown, R. S. Jr. et al., *Nature,* 436 (7053): 973-978, 2005; and Chisari, F. V., *Nature,* 436(7053): 930-932, 2005.

Specifically, the following VX-950 solutions were prepared and stored in capped borosilicate tubes (11.5 mL) at −20° C.:

Stock solution: 961 µg/mL of VX-950 in 2-propanol (10.0 mL)

Diluted stock solution 1: 96.1 µg/ml of VX-950 in 2-propanol (5.00 mL)

Diluted stock solution 2: 9.61 µg/ml of VX-950 in 2-propanol (10.0 mL)

Diluted stock solution 3: 0.961 µg/ml of VX-950 in 2-propanol (10.0 mL)

An internal standard stock solution was prepared to contain 1.00 mg/mL of Compound 1 (a close structural analog of VX-950) in 5.00 mL of 2-propanol, and was stored in a capped borosilicate tube (11.5 ml) at −20° C. A working solution containing the same Compound I was prepared to contain 300 ng/mL of Compound I in 100 mL of acetonitrile, and stored in a capped borosilicate bottle (100 mL) −20° C.

Sample Preparation: 100 µL of plasma and 100 µl, of internal standard working solution (or acetonitrile for blank samples) were added to an extraction tube. After vortex mixing for 30 seconds, 500 µL of toluene was added and extraction was performed by vortex mixing for 30 seconds. After centrifugation at 3000 rpm at 4° C. for 5 minutes, the aqueous layer was frozen in a mixture of acetone and dry ice and the organic layer was transferred to another extraction tube. 50 µL of 2,2-dimethoxypropane was added and the samples were evaporated to dryness under nitrogen at approximately 30° C. The residue was re-dissolved in 300 µL of a mixture of heptane and acetone (90:10, v/v) [or a mixture of heptane and THF (80:20, v/v)] by vortex mixing for 60 seconds. The sample was transferred to an injection vial and an aliquot of 60 µL of the sample was injected into the chromatographic system for analysis with the following chromatographic conditions:

Mobile phase: (Isocratic elution) heptane/acetone/methanol (80:19:1, v/v/v)

Make-up solvent: acetonitrile/acetone/methanol/formic acid (40:60:1:1, v/v/v/v)

Column temperature: −1° C.

Flow rate: 1.00 mL/minute (including 0.750 mL/min mobile phase and 0.250 mL/min make-up solvent, completely transferred to detector)
Injection volume: 60 µL
Auto-sampler temperature: 3° C.

EXAMPLE 8

Combination Therapy with VX-950

A V-950 combination therapy was conducted to determine the safety of VX-950 and its antiviral response. Specifically, this study included 12 treatment-naïve patients infected with genotype 1 HCV. All patients received VX-950 (750 mg q8h), peginterferon alfa-2a ("PEG-IFN", 180 µg weekly), and ribavirin (1000 or 1200 mg daily), for a period of 28 days. At the completion of the 28 days, patients began off-study follow-on therapy with peginterferon alfa-2a and ribavirin under the clinical care of their physicians. Additional HCV RNA assessments were performed at the discretion of the treating physicians during the peginterferon alfa-2a/ribavirin therapy. These included assessments at 4, 8, 14 weeks post-study treatment and later timepoints.

The results show that the VX-950/peginterferon/ribavirin combination was well tolerated in the 28-day study, with no serious adverse events. The observed adverse event profile was consistent with the profile commonly seen with the peginterferon/ribavirin combination therapy. All patients demonstrated a response to the study drug regimen, indicating a rapid and substantial antiviral effect of VX-950. Specifically, 2 patients reached undetectable (<10 IU/mL, Roche TAQMAN™ Assay) levels of plasma HCV RNA within 8 days from the start of dosing, and all patients had undetectable HCV RNA at the end of the 28-day study dosing period. At 12 weeks of follow-on therapy (with peginterferon/ribavirin) after completing the 28-day study dosing, the HCV RNA levels remain undetectable in 11 patients. All patients continued on peginterferon/ribavirin therapy, and were followed for response in accordance with standard practice. Seven patients received a total of 48 weeks of treatment and achieved sustained viral response (SVR). One patient received peginterferon/ribavirin for only 18 weeks (total treatment 22 weeks) before discontinuing, but also achieved SVR. Two patients had viral breakthroughs at 12 weeks and 24 weeks of treatment and two patients have been lost to follow up. In total, 8 out of 10 patients from whom the results were available, achieved SVR. The side effect profile observed during the post-study dosing was consistent with the expected profile of peginterferon/ribavirin therapy.

The observation that SVR was achieved in eight patients, including 1 who completed only 22 weeks of treatment, indicates that VX-950-based regimens may allow increased SVR rates as compared to current therapies.

The current treatment for patients with genotype 1 chronic HCV usually consists of 48 weeks of therapy with only pegylated interferon-alfa-2a/2b (peginterferon alfa-2a) and ribavirin, which results in SVR in only about 50% of patients with genotype-1 HCV and the patients generally show poor tolerability of the treatments.

EXAMPLE 9

Phase 1b Studies

VX-950 had rapid and profound antiviral activity as a single agent or in combination with peginterferon alfa-2a, and was well tolerated for 14 days. This study was designed to provide information on the kinetics of HCV following treatment with VX-950 and peginterferon alfa-2a administered over 14 days.

This study randomized twenty treatment-naïve patients with chronic genotype 1 hepatitis C infection to three dosing arms (Table 6). At the completion of the 14-day study, 19 of 20 patients chose to begin peginterferon alfa-2a/ribavirin, starting within 5 days of completing the 14-day dosing period; as the other one declined to take the combination of Peg-IRN-2a and ribavirin. Clinic visits were conducted at the discretion of the investigators, after completion of the 1-week and 12-week study-mandated follow-up visits. Nineteen patients have been followed through 24 weeks after the completion of the study dosing. After discussion with the treating physicians, ten (4 in VX-950 and 6 in VX-950/peginterferon alfa-2a) patients stopped peginterferon alfa-2a/ribavirin treatment at 24 weeks. The current disposition of the patients is presented in Table 6 below.

TABLE 6

Disposition of Patients

| | Placebo + PegIFN-2a N | Telaprevir N | Telaprevir + PegIRN-2a N | Total N |
|---|---|---|---|---|
| Enrolled | 4 | 8 | 8 | 20 |
| Dosed | 4 | 8 | 8 | 20 |
| Completed 2 Weeks of Treatment | 4 | 8 | 8 | 20 |
| Off Study Treatment (PegIFN-2a/RBV) | | | | |
| Completed 1-Week Safety Follow-up On-Study | 4 | 8 | 8 | 20 |
| Completed 12-Week Antiviral Follow-up On-Study | 4 | 7 | 8 | 19 |
| Completed 24-Week Antiviral Follow-up Off-Study | 4 | 7 | 8 | 19 |
| Peg-IFN-2a/RBV Discontinuation at 24 weeks due to decision of the patients | 0 | 4 | 6 | 10 |

At the last off-study follow-up day (12 weeks after the last on-study follow-up), HCV RNA levels were undetectable in all patients who continued with peginterferon alfa-2a/ribavirin, initially randomized in the VX-950 alone and VX-950/peginterferon alfa-2a groups. The data are provided below in Table 7.

TABLE 7

Undetectable HCV RNA by groups during the post study-treatment period

| | HCV RNA below limit of quantitation[a] (30 IU/mL) n Peg-IFN-2a/RBV On-Study | | HCV RNA below limit of detection[a] (10 IU/mL) n Peg-IFN-2a/RBV On-Study | | HCV RNA below Undetectable[b] n Peg-IFN-2a/RBV Off-Study |
|---|---|---|---|---|---|
| | 1-week F/U | 12-week F/U | 1-week F/U | 12-week F/U | 24-week F/U (12 weeks after last on-study follow-up) |
| VX-950 (N-7) | 3 | 6 | 1 | 5 | 7 |
| VX-950/Peg-IFN-2a (N-8) | 6 | 8 | 3 | 8 | 8 |

TABLE 7-continued

Undetectable HCV RNA by groups during the post study-treatment period

| | HCV RNA below limit of quantitation[a] (30 IU/mL) n Peg-IFN-2a/RBV On-Study | | HCV RNA below limit of detection[a] (10 IU/mL) n Peg-IFN-2a/RBV On-Study | | HCV RNA below Undetectable[b] n Peg-IFN-2a/RBV Off-Study |
|---|---|---|---|---|---|
| | 1-week F/U | 12-week F/U | 1-week F/U | 12-week F/U | 24-week F/U (12 weeks after last on-study follow-up) |
| Peg-IFN-2a (N-4) | 0 | 3 | 0 | 1 | 3 |

[a]COBAS Taqman HCV RNA assay, Roche Molecular Diagnostics
[b]Taqman HCV RNA assay (15 IU/mL) and 5 IU/mL): off-study As shown below in Table 8, of the 10 patients who stopped post-study peginterferon alfa-2a/ribavirin treatment after 24 weeks total treatment, 2 of 4 patients who originally received VX-950 alone demonstrated undetectable plasma HCV RNA level at 12 weeks follow-up after stopping peginterferon alfa-2a; 5 of 6 patients who originally received VX-950/peginterferon alfa-2a demonstrated undetectable plasma HCV RNA level at 12 weeks follow-up after stopping peginterferon alfa-2a

TABLE 8

Undetectable HCV RNA by groups following peginterferon alfa-2a/ribavirin discontinuation

| | Undetectable HCV RNA at 24-week off study peg-IGN-2a/RBV treatment N | Patients who stopped peg-IFN-2a/RBV at Week 24 n/N | Undetectable HCV RNA at 12 weeks follow-up after stopping peg-IFN-2a/RBV n/N |
|---|---|---|---|
| VX-950 (N-7) | 7* | 4/7 | 2/4 |
| VX-950/Peg-IFN-2a (N-8) | 8 | 6/8 | 5/6 |
| Peg-IFN-2a (N-4) | 3 | 0/4 | N/A |

*One patient declined peginterferon alfa-2a/ribavirin.

At 24-week off-study follow-up, all the patients who were initially randomized in VX-950 groups and continued with peginterferon alfa-2a/ribavirin, maintained undetectable HCV RNA. The early (12-week) post-treatment (peginterferon alfa-2a/ribavirin) follow-up viral toad data were consistent with models, suggesting the required duration to achieve SVR was related to the kinetics of early viral clearance. SVR was achieved in 10 of 15 patients who received 14 days of therapy of VX-950 optionally in combination with Peg-INF, followed by Peg-INF/ribavirin for an additional 22 or 46 weeks.

At week 12, all 8 patients who received an initial combination of VX-950 with peginterferon and 5 of 7 patients who received VX-950 alone had undetectable HCV RNA. At week 24, all 15 patients who received VX-950 had undetectable HCV RNA. 10 patients (6 of 8 VX-950 with peginterferon and 4 of 7 VX-950 alone) decided to stop peginterferon/ribavirin at week 24 and 5 patients continued treatment of peginterferon/ribavirin for a total of 48 weeks. All groups were followed for an additional 24 weeks. In patients who received at least 14 days of VX-950 (alone or in combination with peginterferon) before starting the peginterferon with ribavirin, 7 of 10 patients treated for 24 weeks and 3 of 5 patients treated for 48 weeks achieved SVR.

EXAMPLE 10

Phase 2 Study of Telaprevir Administered q8h or q12h with Peginterferon-Alfa-2a or -Alfa-2b and Ribavirin in Treatment-Naïve Subjects with Genotype 1 Hepatitis C: Week 4 Interim Results Background: Study 0208 is an ongoing open-label, randomized Phase 2 study of telaprevir (TVR) administered q8h or q12h in combination with peginterferon-alfa-2a (peginterferon-alfa-2a) or peginterferon-alfa-2b and ribavirin (T/PR) in treatment-naïve subjects with HCV genotype 1 infection. We report the results of an interim analysis conducted at week 12 of treatment.

Methods: 161 subjects were randomized into 4 arms as shown in Table 9.

TABLE 9

| | N | Peg-IFN | TVR | Ribavirin | RVR |
|---|---|---|---|---|---|
| A | 40 | alfa-2a (180 μg/wk) | 750 mg q8h | 1000-1200 mg/d | 82% |
| B | 42 | alfa-2b (1.5 μg/kg/wk) | 750 mg q8h | 800-1200 mg/d | 71% |
| C | 40 | alfa-2a (180 μg/wk) | 1125 mg q12h | 1000-1200 mg/d | 85% |
| D | 39 | alfa-2b (1.5 μg/kg/wk) | 1125 mg q12h | 800-1200 mg/d | 68% |

Subjects in all arms received T/PR treatment for 12 weeks, and will subsequently receive either 12 or 36 additional weeks of PR based on rapid virologic response (RVR) criterion. Subjects who met the definition of viral breakthrough (≥1-log increase in HCV RNA above nadir) discontinued TVR dosing and will complete 48 weeks of PR. An intent-to-treat analysis was performed when all treated subjects had completed week 4 of treatment or had discontinued earlier than week 4. The analysis also assessed all treatment or TVR dosing discontinuations including subjects who discontinued beyond week 4, up to the time of data cutoff. The proportion of subjects with HCV RNA below the limit of detection (TaqMan assay LOD 10 IU/mL) at week 4 (RVR) is reported.

Results: Baseline characteristics were balanced across arms. Although differences did not reach statistical significance, a higher rate of HCV RNA clearance was observed at week 4 in arms A and C compared with arms B and D. The proportion of subjects with undetectable HCV RNA at week 4 was 82% and 85% for arms A and C, respectively; and 71% and 68% for arms B and D, respectively. Up to week 4, the number of subjects with viral breakthrough was 0 and 2 in arms A and C, respectively; and 2 and 1 in arms B and D, respectively. The overall proportion of TVR discontinuations for any reason was 12% (n=19). Similar discontinuation rates were observed in each of the arms.

Conclusions: In the context of the two currently available standard-of-care regimens, TVR 750 mg q8h or 1125 mg q12h in combination with PR yielded high rates of virological response and low viral breakthrough at week 4. Differences in the proportion of subjects with undetectable HCV RNA were observed between arms receiving different PR regimens. Future results from a week 12 interim analysis will further assess the therapeutic potential of TVR q12h dosing, as well as potential differences in efficacy related to the combination of TVR with either peginterferon-alfa-2a or peginterferon-alfa-2b and ribavirin.

TABLE 10

Demographics and Baseline Characteristics

| Parameter | q8h alfa-2a (n = 40) | q8h alfa-2b (n = 42) | q12h alfa-2a (n = 40) | q12h alfa-2b (n = 39) | Total (N = 161) |
|---|---|---|---|---|---|
| Male, n (%) | 20 (50) | 20 (48) | 21 (53) | 19 (49) | 80 (50) |
| Mean age, years (SD) | 45.1 (9.3) | 44.8 (10.5) | 40.0 (9.9) | 47.4 (10.2) | 44.3 (10.2) |
| Caucasian, n (%) | 36 (90) | 38 (91) | 36 (90) | 35 (92) | 145 (91) |
| Median BMI, kg/m$^2$ (range) | 23.4 (19-35) | 23.9 (20-37) | 23.8 (18-34) | 24.7 (20-46) | 24.0 (18-46) |
| Mean ALT, IU/mL (SD) | 79.1 (67.6) | 99.5 (78.6) | 86.0 (56.2) | 88.0 (66.0) | 88.3 (67.1) |
| Baseline HCV RNA | | | | | |
| log$_{10}$ IU/mL, mean (SD) | 6.32 (0.633) | 6.45 (0.657) | 6.39 (0.620) | 6.46 (0.752) | 6.41 (0.663) |
| ≥800,000 IU/mL, n (%) | 29 (73) | 35 (83) | 33 (83) | 33 (85) | 130 (81) |
| HCV genotype, n (%)* | | | | | |
| 1a | 15 (37.5) | 19 (45.2) | 20 (50.0) | 17 (43.6) | 71 (44.1) |
| 1b | 18 (45.0) | 18 (42.9) | 15 (37.5) | 18 (46.2) | 69 (42.9) |
| 1 (subtype undertermined) | 7 (17.5) | 5 (11.9) | 5 (12.5) | 4 (10.3) | 21 (13.0) |

*Determined by TRUGENE HCV 5'NC genotyping assay (Siemens Medical Solutions Diagnostics)

TABLE 11

AEs Reported in >25% of Subjects in Any Group (Regardless of Severity or Causality)

| AE, n (%) | q8h alfa-2a (n = 40) | q8h alfa-2b (n = 42) | q12h alfa-2a (n = 40) | q12h alfa-2b (n = 39) |
|---|---|---|---|---|
| Anemia | 18 (45) | 14 (33) | 14 (35) | 19 (49) |
| Pruritus | 16 (40) | 21 (50) | 19 (48) | 22 (56) |
| Rash | 26 (65) | 15 (36) | 16 (40) | 14 (36) |
| Diarrhea | 10 (25) | 9 (21) | 12 (30) | 13 (33) |
| Nausea | 18 (45) | 14 (33) | 16 (40) | 22 (56) |
| Vomiting | 7 (18) | 5 (12) | 7 (18) | 12 (31) |
| Asthenia | 11 (28) | 16 (38) | 7 (18) | 14 (36) |
| Fatigue | 15 (38) | 15 (36) | 14 (35) | 15 (39) |
| Influenza-like illness | 15 (38) | 19 (45) | 11 (28) | 20 (51) |
| Pyrexia | 8 (20) | 14 (33) | 8 (20) | 11 (28) |
| Decreased appetite | 8 (20) | 4 (10) | 6 (15) | 15 (39) |
| Headache | 13 (33) | 18 (43) | 13 (33) | 16 (41) |

EXAMPLE 11

Phase 2 Study of Telaprevir Administered q8h or q12h with Peginterferon-Alfa-2a or -Alfa-2b and Ribavirin in Treatment-Naïve Subjects with Genotype 1 Hepatitis C: Week 12 Interim Results Telaprevir (TVR) is a potent and selective inhibitor of the HCV NS3.4A protease with demonstrated activity in both treatment-naïve patients and patients who failed prior therapy, including null responders to peginterferon (Peg-IFN) and ribavirin (RBV). In Phase 2 studies in treatment-naïve, HCV genotype 1-infected patients, a 24-week TVR-containing regimen delivered a significant improvement in sustained virologic response rates over current 48-week therapy with peginterferon and ribavirin: PROVE1: 61% versus 41% (p=0.02); PROVE2: 69% versus 46% (p=0.01).

The objective of the C208 study (VX950-TiDP24-C208) is to explore the efficacy, safety, tolerability and pharmacokinetics of TVR, administered as 750 mg q8h or 1125 mg q12h, in combination with peginterferon alfa-2a or peginterferon alfa-2b plus ribavirin (T/PR).

We report results from an interim analysis of C208 conducted at Week 12 of treatment.

C208 is an ongoing, open-label, randomized, multicenter, Phase 2 exploratory study. Adult, treatment-naïve subjects with chronic HCV genotype 1 infection were enrolled, including subjects with bridging fibrosis. Inclusion criteria were consistent with those used in prior HCV studies. Subjects received 12 weeks of T/PR, followed by either 12 or 36 additional weeks of PR based on extended rapid virologic response (RVR) criterion (FIG. 1). Subjects with HCV RNA>1000 IU/mL at Week 4, 6 or 8 were required to discontinue TVR dosing and complete 48 weeks of PR.

An interim intent-to-treat (ITT) analysis was performed and is presented in this report, which includes data obtained for all subjects randomized had completed week 12 of treatment or had discontinued earlier. The primary efficacy endpoint was the proportion of subjects with HCV RNA below the limit of detection (LOD, 10 IU/mL) at different timepoints throughout the first 12 weeks of dosing. HCV RNA levels were measured using the TAQMAN™ HCV RNA assay v2.0 (Roche Molecular Systems Inc., Branchburg, N.J., U.S.A.).

Assessment of virologic breakthrough (defined as a >1-log 10 increase in HCV RNA from nadir, or HCV RNA>100 IU/mL in subjects whose HCV RNA had previously become undetectable [<10 IU/mL] at all assessment timepoints) was performed. Pharmacokinetics and viral dynamics were assessed by pre-defined serial measurements of plasma concentrations of TVR and HCV RNA, respectively, from baseline to Week 12. Pharmacokinetic analysis of TVR was performed using non-compartmental methods for data from full pharmacokinetic profiles. A viral dynamics model, which included fixed effects for treatment and random effects for clearance, drug effect, drop and death rate in infected cells with unstructured variance covariance matrix, was also constructed. Safety and tolerability were assessed by monitoring adverse events (AEs), laboratory abnormalities and cardiovascular parameters.

A total of 9 subjects (5.6%) experienced viral breakthrough (vBT) while on TVR across all arms of the study, of which: this occurred within the first 4 weeks of treatment for 4 subjects; no patients achieved undetectable HCV RNA (<10 IU/mL) before meeting vBT criteria; 1 patient was in the q8hr alfa-2a arm, 3 in the q8hr alfa-2b arm, 2 in the q12 hr alfa-2a arm, and 3 in the q12 hr alfa-2b arm; and 8 patients were infected with HCV genotype 1a. Using population sequencing, none of the patients had TVR-resistance associated mutations at baseline. Where mutations were confirmed, all were previously described TVR-resistance associated mutations (V36M, R155K).

2 additional breakthroughs occurred after discontinuation of TVR, both in patients infected with genotype 1a.

One genotype 1a-infected patient, from the q8h alfa-2b group, had a R155K mutation at baseline by population sequencing. This patient achieved undetectable HCV RNA (<10 IU/mL) at weeks 4 and 12.

No statistically significant differences were noted between TVR-containing regimens with q8h and q12h dosing. Serious AEs leading to permanent treatment discontinuation were mainly due to rash- and anemia-related events.

The majority of laboratory abnormalities were Grade 1 or 2 in severity. Treatment-emergent Grade 3 laboratory abnormalities reported in >2 subjects in the total study population were observed for low white blood cell count (n=32, 11.4%), uric acid (n=14, 5.0%), hemoglobin (n=15, 9.4%), lymphocytes (n=19, 6.8%) and neutrophils (n=33, 11.7%). Grade 3 anemia (hemoglobin <8.5 g/dL) occurred in 12 (7.5%) patients. Erythropoetin was used in 33 (20%) subjects in the total population at the discretion of the investigator.

No relevant changes were seen in electrocardiographic or vital signs parameters.

anemia, and were comparable across the telaprevir q12 hr and telaprevir q8 hr regimens. Total exposure ($AUC_{24\,h}$) to telaprevir was similar across regimens. On average, telaprevir $C_{max}$ was higher and $C_{min}$ was lower for the telaprevir q12h versus telaprevir q8h dosing schedules.

TABLE 12

| T dosing in T/PR regimens | HCV RNA undetectable at wk 12 n/N (%) | | | |
|---|---|---|---|---|
| | Overall | Genotype 1a | Genotype 1b | Baseline HCV RNA >800,000 IU/mL n/N (%) |
| T 750 mg q8h (n = 82) | 76/82 (93) | 29/34 (85) | 36/36 (100) | 58/64 (91) |
| T 1125 mg q12h (n = 79) | 66/79 (84) | 30/37 (81) | 30/33 (91) | 56/66 (85) |

TABLE 13

Treatment Discontinuations for All Drugs During the First 12 Weeks of Treatment

| Treatment discontinuations, n (%) | q8h alfa-2a (n = 40) | q8h alfa-2b (n = 42) | q12h alfa-2a (n = 40) | q12h alfa-2b (n = 39) | Total (N = 161) |
|---|---|---|---|---|---|
| Any reason | 6 (15) | 4 (10) | 6 (15) | 8 (21) | 24 (15) |
| Due to AEs | 4 (10) | 2 (5) | 4 (10) | 3 (8) | 13 (8) |
| Due to subjects reaching virologic endpoint | 1 (3) | 2 (5) | 1 (3) | 3 (8) | 7 (4) |
| Withdrawal of consent | 1 (3) | 0 | 1 (3) | 1 (3) | 3 (2) |
| Other | 0 | 0 | 0 | 1 (3) | 1 (1) |

TABLE 14

| | Mean Pharmacokinetic Parameters for TVR at Week 8 | | | |
|---|---|---|---|---|
| | q8h alfa-2a (n = 40) | q8h alfa-2b (n = 42) | q12h alfa-2a (n = 40) | q12h alfa-2b (n = 39) |
| $AUC_{24h}$, ng · h/mL ± SD | 85860 ± 14961 | 80760 ± 9042 | 81620 ± 20140 | 78580 ± 12126 |
| $C_{max}$, ng/mL ± SD | 4523 ± 768 | 4054 ± 750 | 4882 ± 784 | 4248 ± 656 |
| $C_{min}$, ng/mL ± SD | 2624 ± 507 | 2569 ± 453 | 2134 ± 620 | 2321 ± 384 |

There was no difference in efficacy, safety and PK parameters between the four telaprevir therapeutic regimens studied.

A high proportion of subjects achieved undetectable HCV RNA (<10 or <25 IU/mL) with all four telaprevir-containing regimens.

All treatment groups achieved rapid suppression of HCV RNA. At Week 4: 87-96% of subjects achieved <25 IU/mL HCV RNA; 67-83% of subjects achieved <10 IU/mL HCV RNA. At Week 12: 83-93% of subjects achieved <10 IU/mL HCV RNA. Low rates of vBT (n=9; 5.6%) were observed while patients were receiving TVR/PR.

AEs were similar in type and frequency to those seen with peginterferon and ribavirin, with the exception of rash and All of the documents cited herein, are incorporated herein by reference.

Other Embodiments

While a number of embodiments and examples of this invention are described herein, it is apparent that these embodiments and examples may be altered to provide additional embodiments and examples which utilize the pharmaceutical formulations and drug regimens of this invention. Therefore, it will be appreciated that the scope of this invention is to be defined by the appended claims rather than by the specific embodiments that have been represented by way of example above.

What is claimed is:

1. A therapeutic regimen comprising administering to a patient infected with the hepatitis C virus peginterferon and ribavirin with VX-950 in an initial phase and administering peginterferon and ribavirin over a secondary phase, wherein the secondary phase occurs after the initial phase, and wherein the VX-950 administered in the initial phase is in an amount of 1125 mg twice per day, the peginterferon administered in the initial phase and in the secondary phase is in an amount of 180 micrograms per week and the ribavirin administered in the initial phase and in the secondary phase is in an amount of 1000 to 1200 mg per day.

2. The therapeutic regimen of claim 1, wherein at least 65% of patients have undetectable HCV RNA levels at week 4.

3. The therapeutic regimen of claim 2, wherein at least 75% of patients have undetectable HCV RNA levels at week 4.

4. The therapeutic regimen of claim 3, wherein at least 80% of patients have undetectable HCV RNA levels at week 4.

5. The therapeutic regimen of claim 4, wherein at least 85% of patients have undetectable HCV RNA levels at week 4.

6. The therapeutic regimen of claim 1, wherein at least 80% of patients have undetectable HCV RNA levels at week 12.

7. The therapeutic regimen of claim 6, wherein at least 84% of patients have undetectable HCV RNA levels at week 12.

8. The therapeutic regimen of claim 7, wherein at least 90% of patients have undetectable HCV RNA levels at week 12.

9. The therapeutic regimen of claim 8, wherein at least 93% of patients have undetectable HCV RNA levels at week 12.

10. The therapeutic regimen of claim 1, wherein VX-950 is administered every 12 hours.

11. The therapeutic regimen of claim 1, wherein the peginterferon administered in the initial phase and in the secondary phase is peginterferon alfa 2a.

12. The therapeutic regimen of claim 1, wherein the initial phase is for 12 weeks.

13. The therapeutic regimen of claim 1, wherein the secondary phase is for 12 weeks or 36 weeks.

14. A therapeutic regimen comprising administering to a patient infected with the hepatitis C virus peginterferon and ribavirin with VX-950 in an initial phase and administering peginterferon and ribavirin over a secondary phase, wherein the secondary phase occurs after the initial phase, and wherein the VX-950 administered in the initial phase is in an amount of 1125 mg twice per days, the peginterferon administered in the initial phase and in the secondary phase is in an amount of 1.5 micrograms per kilogram per week and the ribavirin administered in the initial phase and in the secondary phase is in an amount of 1000 to 1200 mg per day.

15. The therapeutic regimen of claim 14, wherein at least 65% of patients have undetectable HCV RNA levels at week 4.

16. The therapeutic regimen of claim 15, wherein at least 75% of patients have undetectable HCV RNA levels at week 4.

17. The therapeutic regimen of claim 16, wherein at least 80% of patients have undetectable HCV RNA levels at week 4.

18. The therapeutic regimen of claim 17, wherein at least 85% of patients have undetectable HCV RNA levels at week 4.

19. The therapeutic regimen of claim 14, wherein at least 80% of patients have undetectable HCV RNA levels at week 12.

20. The therapeutic regimen of claim 19, wherein at least 84% of patients have undetectable HCV RNA levels at week 12.

21. The therapeutic regimen of claim 20, wherein at least 90% of patients have undetectable HCV RNA levels at week 12.

22. The therapeutic regimen of claim 21, wherein at least 93% of patients have undetectable HCV RNA levels at week 12.

23. The therapeutic regimen of claim 14, wherein VX-950 is administered every 12 hours.

24. The therapeutic regimen of claim 14, wherein the peginterferon administered in the initial phase and in the secondary phase is peginterferon alfa 2b.

25. The therapeutic regimen of claim 14, wherein the initial phase is for 12 weeks.

26. The therapeutic regimen of claim 14, wherein the secondary phase is for 12 weeks or 36 weeks.

* * * * *